United States Patent
Berthel et al.

(10) Patent No.: US 7,902,248 B2
(45) Date of Patent: Mar. 8, 2011

(54) OXIME GLUCOKINASE ACTIVATORS

(75) Inventors: Steven Joseph Berthel, Mendham Township, NJ (US); Robert Francis Kester, West Orange, NJ (US); Douglas Eric Murphy, San Diego, NJ (US); Thomas Jay Prins, San Diego, CA (US); Frank Ruebsam, San Diego, CA (US); Chinh Viet Tran, San Diego, CA (US); Dionisios Vourloumis, Athens (GR)

(73) Assignee: Hoffmann-La Roche Inc., Nutley, NJ (US)

( * ) Notice: Subject to any disclaimer, the term of this patent is extended or adjusted under 35 U.S.C. 154(b) by 473 days.

(21) Appl. No.: 11/999,670

(22) Filed: Dec. 6, 2007

(65) Prior Publication Data

US 2008/0146625 A1 Jun. 19, 2008

Related U.S. Application Data

(60) Provisional application No. 60/874,913, filed on Dec. 14, 2006.

(51) Int. Cl.
*A61K 31/415* (2006.01)
*A61K 31/428* (2006.01)
*C07D 231/10* (2006.01)
*C07D 277/20* (2006.01)

(52) U.S. Cl. ......... 514/407; 548/356.1; 548/371.4; 548/371.7; 548/146; 548/161; 514/367; 514/403; 514/406

(58) Field of Classification Search ........ 548/146, 548/161, 164, 356.1, 371.7; 514/367, 403, 514/406, 407
See application file for complete search history.

(56) References Cited

U.S. PATENT DOCUMENTS

| 6,353,111 | B1 | 3/2002 | Corbett et al. |
| 6,951,945 | B2 * | 10/2005 | Bizzarro et al. ............ 548/127 |
| 7,132,425 | B2 * | 11/2006 | Chen et al. ............ 514/255.05 |
| 7,259,166 | B2 * | 8/2007 | Corbett et al. .......... 514/255.05 |
| 7,514,439 | B2 * | 4/2009 | Sugawara et al. ........ 514/254.02 |
| 2004/0138465 | A1 | 7/2004 | Spurr |

FOREIGN PATENT DOCUMENTS

| DE | 4426940 | 1/1996 |
| DE | 19925780 | 2/2000 |
| EP | 282971 | 12/1994 |
| WO | WO 9526956 | 10/1995 |
| WO | WO 9623763 | 8/1996 |
| WO | WO 9700866 | 1/1997 |
| WO | WO 2001044216 | 6/2001 |
| WO | WO 2002008209 | 1/2002 |
| WO | WO 2002014312 | 2/2002 |
| WO | WO 2004052869 A1 | 6/2004 |
| WO | WO 2004058724 | 7/2004 |
| WO | WO 2004063179 | 7/2004 |
| WO | WO 2004063194 | 7/2004 |
| WO | WO 2004072031 | 8/2004 |
| WO | WO 2004072066 | 8/2004 |
| WO | WO 2005023761 | 3/2005 |
| WO | WO 2005103021 | 11/2005 |
| WO | WO 2006016194 | 2/2006 |
| WO | WO 2007007886 | 1/2007 |
| WO | WO 2007026761 | 3/2007 |
| WO | WO 2007058990 | 5/2007 |
| WO | WO 2007146712 | 12/2007 |

OTHER PUBLICATIONS

Komori et al (2004): STN International HCAPLUS database, (Columbus, Ohio), Accession No. 2004:162673.*
Ishikawa, T.; Kamiyama, *Antibiot.* 2000, 53, 1071-1085.
Kai, H.; Matsumoto, *Bioorg. Med. Chem. Lett.* 2001, 11, 1997-2000.
Yamashita, T.; *Synlett.* 2003, 738-740.
Domagala, *J. Org. Chem.* 1981, 46, 134-140.
Yamazaki, *Bioorganic & Medicinal Chemistry* 2005, 13, 2509-2522.
Jordan, A. D.; *J. Org. Chem.* 2003, 68, 8693-8696.
Johnson, F. E.; Hamilton, C. S. *J. Am. Chem. Soc.* 1949, 71, 74-6.
Expert Opin. Ther.Patents (2008) 18(7) p. 759.
Nippon Noyaku Gakkaishi (2000) 24-30.
Tet. Lett. 2006, 2675.

* cited by examiner

*Primary Examiner* — Golam M Shameem
(74) *Attorney, Agent, or Firm* — George W. Johnston; Dennis P. Tramaloni; Samuel H. Megerditchian

(57) ABSTRACT

Disclosed herein are pyrazole glucokinase activators of the formula (I):

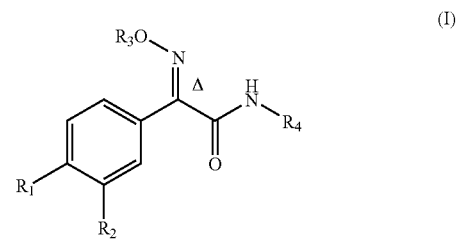

that are useful for the treatment of metabolic diseases and disorders.

19 Claims, No Drawings

OXIME GLUCOKINASE ACTIVATORS

PRIORITY TO RELATED APPLICATION(S)

This application claims the benefit of U.S. Provisional Application No. 60/874,913, filed Dec. 14, 2006, which is hereby incorporated by reference in its entirety.

FIELD OF THE INVENTION

The invention is directed to compounds of the formula (I):

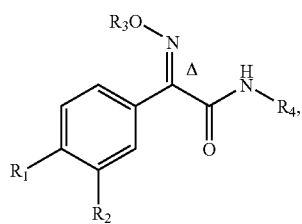

(I)

and to pharmaceutical compositions comprising said compounds. The compounds and compositions disclosed herein are glucokinase activators useful for the treatment of metabolic diseases and disorders, preferably diabetes mellitus, more preferably type II diabetes mellitus.

All documents cited or relied upon below are expressly incorporated herein by reference.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J.*, 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion and suppression of hepatic glucose production respectively. Such agents would be useful for treating type II diabetes.

SUMMARY OF THE INVENTION

In an embodiment of the present invention, provided is a compound of formula (I):

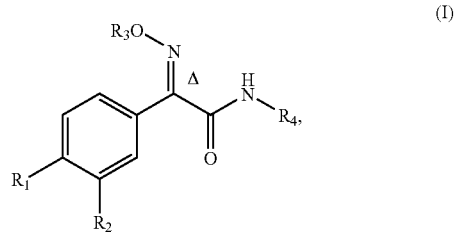

(I)

wherein:

$R_1$, $R_2$ are, independently, hydrogen, halo, amino, hydroxyamino, cyano, nitro, lower alkyl, —$OR_5$, —C(O)$OR_6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, lower alkoxy lower alkyl sulfinyl, perfluoro-lower alkyl sulfinyl or sulfonamido;

$R_3$ is cycloalkyl, having from 3 to 7 carbon atoms, or lower alkyl;

$R_4$ is benzothiazole, unsubstituted or substituted with lower alkyl, halo, alkoxy or oxo, urea, or an unsubstituted or monosubstituted five-or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, said monosubstituted heteroaromatic ring being monosubstituted at a position on a ring carbon atom or nitrogen other than adjacent to said connecting carbon atom with a substituent selected from the group consisting of lower alkyl, halo, nitro, cyano, perfluoro-lower alkyl, oxo, —$(CH_2)_n$—$OR_7$, —$(CH_2)_n$—C(O)—$OR_7$, —$(CH_2)_n$—C(O)—NH—$R_7$, —C(O)C(O)—$OR_7$, —$(CH_2)_n$—, $NHR_7$, —$(CH_2)_m$-

Ph, —(CH$_2$)$_m$-Ph-C(O)OR$_7$, —(CH$_2$)$_m$-Ph-C(O)NH$_2$, —(CH$_2$)$_m$-Ph-NH—C(O)R$_7$ or —(CH$_2$)$_m$-het;

R$_5$ is hydrogen, lower alkyl, or perfluoro-lower alkyl;

R$_6$ is lower alkyl;

R$_7$ is hydrogen or lower alkyl;

n is 0, 1, 2, 3 or 4; wherein n is not zero if a nitrogen-oxygen bond results;

m is 1, 2, 3 or 4;

het is a five- or six-membered heteroaromatic ring; and is a trans configuration across the double bond;

or a pharmaceutically acceptable salt thereof.

In another embodiment of the present invention, provided is a pharmaceutical composition, comprising a therapeutically effective amount of a compound according to formula (I) and a pharmaceutically acceptable carrier.

In a further embodiment of the present invention, provided is a method for treating a metabolic disease and/or disorder, comprising the step of administering a therapeutically effective amount of a compound according to formula (I) to a patient in need thereof.

DETAILED DESCRIPTION OF THE INVENTION

The compounds of formula I have been found to activate glucokinase in vitro. Glucokinase activators are useful for increasing insulin secretion in the treatment of type II diabetes. In accordance with this invention, it has been found that the compounds of formula I having the E configuration across the double bond cause an increase in glucokinase activity. On the other hand, the compounds of formula I having the Z configuration across the double bond do not cause an increase glucokinase activity. When the letter Z is utilized in this application, it designates that the two highest priority substituents attached across the double bond are on the same side of the double bond. The letter E as utilized in this application, designates that the two highest priority substituents attached across the double bond are on opposite sides of the double bond. In the compound of formula I, the symbol "Δ" denotes an E configuration across the double bond.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic (i.e., cycloalkyl) or acyclic, saturated (partially saturated if cyclic) or unsaturated hydrocarbyl radical which may be substituted or unsubstituted. Where cyclic, the alkyl group is preferably C$_3$ to C$_{12}$, more preferably C$_3$ to C$_{10}$, more preferably C$_3$ to C$_7$. Where acyclic, the alkyl group is preferably C$_1$ to C$_{10}$, more preferably C$_1$ to C$_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated (partially saturated if cyclic) or unsaturated hydrocarbyl radical wherein said cyclic lower alkyl group is C$_3$, C$_4$, C$_5$, C$_6$ or C$_7$, and wherein said acyclic lower alkyl group is C$_1$, C$_2$, C$_3$ or C$_4$, and is preferably selected from methyl, ethyl, propyl (n-propyl or isopropyl) or butyl (n-butyl, sec-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

The lower alkyl groups may be substituted or unsubstituted, preferably unsubstituted. Where substituted, there will generally be, for example, 1 to 3 substituents present, preferably 1 substituent.

As used herein, the term "halogen" is used interchangeably with the word "halo", and, unless otherwise stated, designates all four halogens, i.e. fluorine, chlorine, bromine, and iodine. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, the term "lower alkoxy" signifies a lower alkyl group as defined above linked via an oxygen to the remainder of the molecule and includes both straight chain and branched chain alkoxy groups having from 1 to 7 carbon atoms, such as methoxy, ethoxy, propoxy, isopropoxy, preferably methoxy and ethoxy. "Lower alkoxy lower alkyl" signifies a lower alkoxy linked via an oxygen to a lower alkyl group, which is linked to the remainder of the molecule.

As used herein the term "aryl" signifies aryl mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydroxide group of the COOH moiety removed. Among the preferred aroyl groups is benzoyl.

As used herein, —C(O)OR represents,

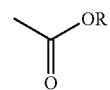

and so forth.

As used herein, the term "urea" is commonly known in the art and is, for example, described in U.S. Pat. No. 6,353,111

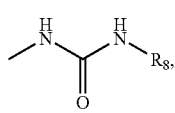

where $R_8$ is H or lower alkyl.

As used herein, the term "heteroaromatic" denotes an unsubstituted or substituted five or six membered heteroaromatic ring having from 1 to 3 heteroatoms selected from the group consisting of oxygen, nitrogen or sulfur. Among the preferred are mono-substituted heteroaromatic rings including, for example, thiazolyl, pyrazolyl, pyridazinyl, pyrazinyl, isoxazolyl, isothiazolyl, pyridinyl, pyrimidinyl, thiadiazolyl, oxazolyl, and imidazolyl.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the hydrogen is replaced with -lower alkyl which is optionally substituted, e.g., with heterocycle, cycloalkyl, etc. Examples of substituted lower alkyl esters are those in which lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —$CONH_2$ is also considered an ester, as the —$NH_2$ may be cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp.108-109; Krogsgaard-Larsen, et. al., Textbook of Drug Design and Development (2d Ed. 1996) at pp. 152-191.

During the course of the reactions provided below in the Reaction Scheme and discussion, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxyl or hydroxyl group. Exemplary ester groups useful for those purposes are those in which the acyl moieties are derived from a lower alkanoic, aryl lower alkanoic, or lower alkane dicarboxylic acid.

Among the activated acids which can be utilized to form such groups are acid anhydrides, acid halides, preferably acid chlorides or acid bromides derived from aryl or lower alkanoic acids. Examples of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

Similarly, the term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2 to 3. Particularly preferred amino protecting groups are t-butyl carbamate (BOC), benzyl carbamate (CBZ), and 9-fluorenylmethyl carbamate (FMOC).

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants.

They can also contain other therapeutically valuable substances, including additional active ingredients other than those of formula I.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

The compounds of the present invention can be prepared by any conventional means. Suitable processes for synthesizing these compounds are provided in the Examples. Generally, compounds of formula I can be prepared according to the Schemes described below. The sources of the starting materials for these reactions are also described.

In accordance with one embodiment of the compound of formula I, are those compounds where $R_3$ is cyclopentyl. Among the various embodiments are included those compounds where $R_4$ is an unsubstituted thiazoles, preferably those compounds where one of said $R_1$ and $R_2$ is halo and the other of said $R_1$ and $R_2$ is lower alkyl sulfonyl.

In accordance with another embodiment of the invention are those compounds where $R_3$ is cyclopentyl and where $R_4$ is a mono-substituted thiazole. Among the embodiments are those compounds where the mono-substitution is —C(O)—$NH_2$. Among the embodiments are those where one of $R_1$ and $R_2$ is halo and the other of said $R_1$ and $R_2$ is lower alkyl sulfonyl.

In accordance with another embodiment of the invention are those compounds where $R_3$ is cyclopentyl and where $R_4$ is a mono-substituted thiazole. Among the embodiments are those compounds where the mono-substitution is lower alkyl. Among the embodiments of these compounds are those compounds where one of $R_1$ and $R_2$ is lower alkyl sulfonyl and the other of $R_1$ and $R_2$ is halo.

In accordance with another embodiment of this invention, where $R_3$ is cyclopentyl and $R_4$ is a mono-substituted [1,2,4]-thiadiazole, are those compounds where the mono-substitution on the [1,2,4]-thiadiazole ring is lower alkyl, preferably where one of $R_1$ and $R_2$ is lower alkyl sulfonyl and the other of $R_1$ and $R_2$ is halo.

In accordance with another embodiment of this invention, where $R_3$ is cyclopentyl and $R_4$ is a mono-substituted [1,2,4]-thiadiazole, are those compounds where the mono-substitution on the [1,2,4]-thiadiazole ring is arylalkyl, preferably where one of $R_1$ and $R_2$ is lower alkyl sulfonyl and the other of $R_1$ and $R_2$ is halo.

In accordance with another embodiment of this invention, where $R_3$ is cyclopentyl and $R_4$ is a mono-substituted [1,3,4]-thiadiazole, are those compounds where the mono-substitution on the [1,3,4]-thiadiazole ring is lower alkyl, preferably where one of $R_1$ and $R_2$ is lower alkyl sulfonyl and the other of $R_1$ and $R_2$ is halo.

In accordance with another embodiment of this invention, where $R_3$ is cyclopentyl and $R_4$ is a mono-substituted [1,3,4]-thiadiazole, are those compounds where the mono-substitution on the [1,3,4]-thiadiazole ring is arylalkyl, preferably where one of $R_1$ and $R_2$ is lower alkyl sulfonyl and the other of $R_1$ and $R_2$ is halo.

In accordance with another embodiment of this invention, where $R_3$ is cyclopentyl and $R_4$ is a mono-substituted benzothiazole, are those compounds where the mono-substitution on the benzothiazole ring is halo, preferably where one of $R_1$ and $R_2$ is lower alkyl sulfonyl and the other of $R_1$ and $R_2$ is halo.

In accordance with another embodiment of this invention, where $R_3$ is cyclopentyl and $R_4$ is a mono-substituted benzothiazole, are those compounds where the mono-substitution on the benzothiazole ring is lower alkoxy, preferably where one of $R_1$ and $R_2$ is lower alkyl sulfonyl and the other of $R_1$ and $R_2$ is halo.

In accordance with another embodiment of this invention, where $R_3$ is cyclopentyl and $R_4$ is an unsubstituted benzothiazole, are preferably those compounds where one of $R_1$ and $R_2$ is lower alkyl sulfonyl and the other of $R_1$ and $R_2$ is halo.

In accordance with another embodiment of this invention, where $R_3$ is cyclopentyl and $R_4$ is an unsubstituted benzothiazole, are preferably those compounds where $R_1$ is lower alkyl sulfonyl.

In accordance with another embodiment of this invention, where $R_3$ is cyclopentyl and $R_4$ is an unsubstituted benzothiazole, are preferably those compounds where $R_1$ and $R_2$ is halo.

In accordance with another embodiment of this invention, where $R_3$ is cyclopentyl and $R_4$ is a mono-substituted pyrazole, are those compounds where the mono-substitution on the pyrazole ring is lower alkyl, are preferably those compounds where $R_1$ and $R_2$ is halo.

In accordance with another embodiment of this invention, where $R_3$ is cyclopentyl and $R_4$ is a mono-substituted pyrazole, are those compounds where the mono-substitution on the pyrazole ring is lower alkyl, preferably where one of $R_1$ and $R_2$ is halo and the other of $R_1$ and $R_2$ is halo or lower alkyl sulfonyl.

In accordance with another embodiment of this invention, where $R_3$ is cyclopentyl and $R_4$ is a mono-substituted pyrazole, are those compounds where the mono-substitution on the pyrazole ring is substituted arylalkyl, preferably where one of $R_1$ and $R_2$ is halo and the other of $R_1$ and $R_2$ is lower alkyl sulfonyl.

In accordance with another embodiment of this invention, where $R_3$ is cyclopentyl and $R_4$ is a mono-substituted pyrazole, are those compounds where the mono-substitution on the pyrazole ring is heteroarylalky, preferably where one of $R_1$ and $R_2$ is halo and the other of $R_1$ and $R_2$ is lower alkyl sulfonyl.

In accordance with another embodiment of this invention, where $R_3$ is cyclopentyl and $R_4$ is an unsubstituted isoxazole, are preferably those compounds where one of $R_1$ and $R_2$ is halo and the other of $R_1$ and $R_2$ is lower alkyl sulfonyl.

In accordance with another embodiment of this invention, where $R_3$ is cyclopentyl and $R_4$ is an unsubstituted pyrazine, are preferably those compounds where one of $R_1$ and $R_2$ is halo and the other of $R_1$ and $R_2$ is lower alkyl sulfonyl.

In accordance with another embodiment of this invention, where R$_3$ is cyclopentyl and R$_4$ is a lower alkyl urea, are preferably those compounds where one of R$_1$ and R$_2$ is halo and the other of R$_1$ and R$_2$ is lower alkyl sulfonyl.

In accordance with another embodiment of formula I, are those compounds where R$_3$ is cyclohexyl. Among the various embodiments of formula I are included those compounds where R$_4$ is a mono-substituted pyrazole. Among the various embodiments included are those compounds where the mono-substitution on the pyrazole ring is lower alkyl, preferably where one of R$_1$ and R$_2$ is halo and the other of R$_1$ and R$_2$ is lower alkyl sulfonyl.

In accordance with another embodiment of this invention, where R$_3$ is cyclohexyl and R$_4$ is an unsubstituted benzothiazole, are preferably those compounds where one of R$_1$ and R$_2$ is halo and the other of R$_1$ and R$_2$ is lower alkyl sulfonyl.

In accordance with another embodiment of this invention, where R$_3$ is cyclohexyl and R$_4$ is a mono-substituted [1,2,4]-thiadiazole are those compounds where the mono-substitution on the [1,2,4]-thiadiazole ring is lower alkyl, preferably where one of R$_1$ and R$_2$ is lower alkyl sulfonyl and the other of R$_1$ and R$_2$ is halo.

In accordance with another embodiment of this invention where R$_3$ is cyclohexyl and where R$_4$ is a mono-substituted thiazole, are those compounds where the mono-substitution is —C(O)—NH$_2$, preferably where one of R$_1$ and R$_2$ is lower alkyl sulfonyl and the other of R$_1$ and R$_2$ is halo.

In accordance with another embodiment of formula I, are those compounds where R$_3$ is isobutyl. Among the various embodiments of compounds are included those compounds where R$_4$ is an unsubstituted benzothiazole, preferably where one of R$_1$ and R$_2$ is halo and the other of R$_1$ and R$_2$ is lower alkyl sulfonyl.

In accordance with another embodiment of this invention where R$_3$ is isobutyl and R$_4$ is a mono-substituted pyrazole, are those compounds where the mono-substitution on the pyrazole ring is lower alkyl, preferably where one of R$_1$ and R$_2$ is halo and the other of R$_1$ and R$_2$ is lower alkyl sulfonyl.

In accordance with another embodiment of formula I, are those compounds where R$_3$ is isopropyl. Among the various embodiments are included those compounds where R$_4$ is an unsubstituted benzothiazole, preferably where one of R$_1$ and R$_2$ is halo and the other of R$_1$ and R$_2$ is lower alkyl sulfonyl.

In accordance with another embodiment of this invention where R$_3$ is isopropyl and R$_4$ is a pyrazole ring. Among the various embodiments are those compounds where the pyrazole ring is unsubstituted or substituted, preferably mono-substituted. Among the mono-substituted compounds, the preferred substitution on the pyrazole ring is lower alkyl, preferably where one of R$_1$ and R$_2$ is halo and the other of R$_1$ and R$_2$ is lower alkyl sulfonyl.

The compound of formula I can be prepared starting from the compound of formula II by the following Reaction Scheme:

Reaction Scheme

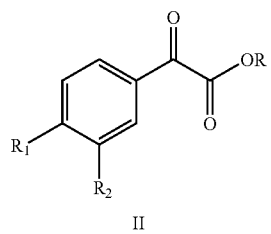

II

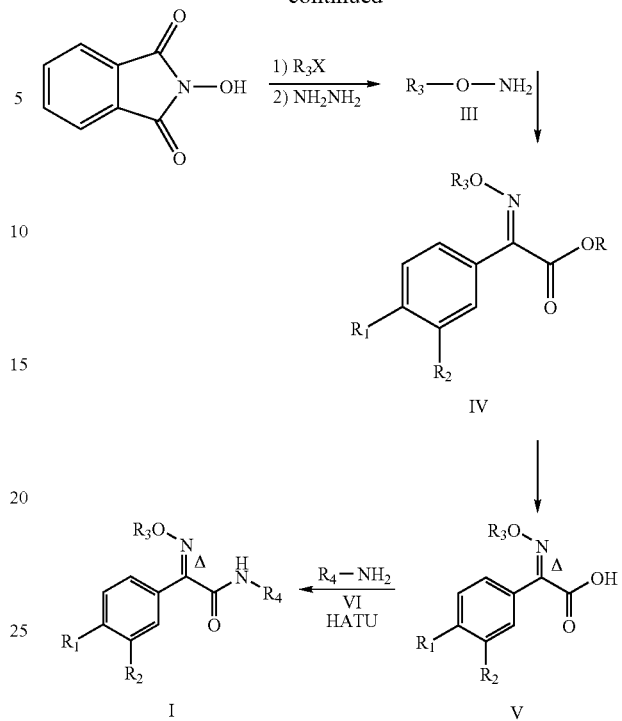

wherein R$_1$, R$_2$, R$_3$ and R$_4$ are as above. R is lower alkyl.

The lower alkyl esters of formula II wherein one of R$_1$ is thiomethyl or methylsulfonyl, and R$_2$ is hydrogen, methyl or chloro are known from the literature (see for example Chen, S.; Corbett, W. L.; Guertin, K. R.; Haynes, N.-E.; Kester, R. F.; Mennona, F. A.; Mischke, S. G.; Qian, Y.; Sarabu, R.; Scott, N. R.; Thakkar, K. C. WO 2004/052869 A1, and references cited therein). The lower alkyl esters of formula II wherein R$_1$ is chloro and R$_2$ is hydrogen or chloro or R$_1$ is hydrogen and R$_2$ is chloro are commercially available. Other lower alkyl esters of formula II are commercially available or can be made by conventional Friedel Crafts chemistry for acylation of aromatic rings (Jilek, J.; Sindelar, K.; Grimova, J.; Maturova, E.; Holubek, J.; Svatek, E.; Metysova, J,; Metys, J.; Hrubantova, M.; Protiva, M. *Coll. Czech. Chem. Comm.* 1990, 55, 1266-77). All the reactions hereto forward are to be carried out on lower alkyl esters of the carboxylic acids of formula II. If desired, the lower alkyl thio compounds can then be converted to the corresponding lower alkyl sulfonyl compounds of formula II by oxidation. Any conventional method of oxidizing alkyl thio substituents to sulfones can be utilized to effect this conversion.

In cases, where only the carboxylic acids are available, they can converted to the corresponding esters of lower alkyl alcohols using any conventional esterification method.

The O-substituted hydroxylamines of formula III can be obtained via O-alkylation of N-hydroxyphthalimide with cycloalkyl halides or lower alkyl halides R$_3$—X followed by removal of the phthalimde protecting group with hydrazine hydrate (see for example Ishikawa, T.; Kamiyama, K.; Matsunaga, N.; Tawada, H.; Iizawa, Y.; Okonogi, K.; Miyake, A. *J. Antibiot.* 2000, 53,1071-1085).

The oximes of formula IV can be prepared by reacting hydroxylamine compounds of formula III with the said lower alkyl esters of formula II (see for example Kai, H.; Matsumoto, H.; Hattori, N.; Takase, A.; Fujiwara, T.; Sugimoto, H. *Bioorg. Med. Chem. Lett.* 2001, 11, 1997-2000 and Yamashita, T.; Tokuyama, H.; Fukuyama, T. *Synlett*. 2003, 738-740). The compounds of formula IV are formed as mixtures of E and Z isomers across the double bond through this condensation reaction. The mixture of E and Z isomers of the compounds of formula IV can be separated by means of column chromatography to obtain the pure E and Z isomers of compounds IV.

The E and Z isomers of compounds of formula IV are hydrolyzed to the acids of formula V where the configuration across the double bond is E or Z respectively. The ester functionality can be hydrolyzed to the acid by lithium hydroxide saponification. The desired E isomer of formula V is identified as such by it relative rate of hydrolysis with respect to the undesired Z isomer (For examples of the formation of O-substituted oximes and stereochemistry determination through chemical reactivity, see Domagala, J. M.; Haskell, T. H.; *J. Org. Chem.* 1981, 46, 134-140).

Compounds of formula V can be condensed with the compounds of formula VI via conventional peptide coupling to produce the desired compounds of formula I wherein the configuration across the double bond is E. In carrying out this reaction, any conventional method of condensing a primary amine with a carboxylic acid can be utilized to effect this conversion. Compounds of formula VI which are 4, 5, 6, or 7 monosubstituted or disubstituted benzothiazoles are commercially available or can be prepared from the corresponding anilines (Yamazaki, K.; Kaneko, Y.; Suwa, K.; Ebara, S.; Nakazawa, K.; Yasuno, K. *Bioorganic & Medicinal Chemistry* 2005, 13, 2509-2522, Jordan, A. D.; Luo, C.; Reitz, A. B. *J. Org. Chem.* 2003, 68, 8693-8696., Johnson, G.; Pavia, M. R. EP 282971) or phenylthioureas (Johnson, F. E.; Hamilton, C. S. *J. Am. Chem. Soc.* 1949, 71, 74-6, Spurr, P. US 2004138465). Compounds of formula VI which are unsubstituted or monosubstituted five-or six-membered heteroaromatic rings are commercially available or can be prepared as previously described (see Chen, S.; Corbett, W. L.; Guertin, K. R.; Haynes, N-E.; Kester, R. F.; Mennona, F. A.; Mischke, S. G.; Qian, Y.; Sarabu, R.; Scott, N. R.; Thakkar, K. C. WO 2004052869 A1; U.S. Provisional Application Ser. No. 60/832,907).

This invention will be better understood from the following examples, which are for purposes of illustration and are not intended to limit the invention defined in the claims which follow thereafter.

EXAMPLES

Example 1

(E)-2-(3-Chloro-4-methanesulfonyl-phenyl)-2-cyclopentyloxyimino-N-(1-methyl-1H-pyrazol-3-yl)-acetamide

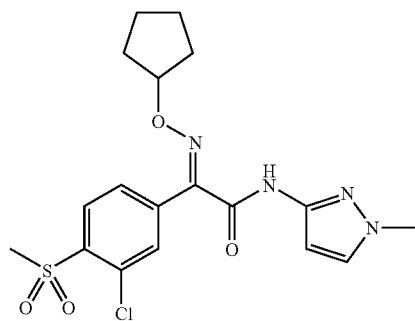

(3-Chloro-4-methylsulfanyl-phenyl)-oxo-acetic acid methyl ester (prepared as in PCT WO 2004/052869 A1, Example 1, 1.89 g, 7.72 mmol) and oxone (14.26 g, 23.3 mmol) were combined in a mixture of water (4 mL) and methanol (40 mL) and stirred for 4 h. The methanol was evaporated in vacuo and the remaining mixture was treated with water (30 mL) and extracted with ethyl acetate (3×40 mL). The combined organic phases were dried over magnesium sulfate and evaporated in vacuo. The residue was purified by flash column chromatography (Merck silica gel 60, 40-63 μm; 50% ethyl acetate/hexanes) to afford (3-chloro-4-methanesulfonyl-phenyl)-oxo-acetic acid methyl ester (1.27 g, 60%) as a white solid: $H^1$-NMR (400 MHz, $CDCl_3$) δ=3.32 (3H, s), 4.03 (3H, s), 8.14 (1H, dd, J=8.0 Hz, J=1.6 Hz), 8.23 (1H, d, J=1.6 Hz), 8.30 (1H, d, J=8.0 Hz).

Solid potassium carbonate (8.64 g, 62.5 mmol) was added to a solution of N-hydroxyphthalimide (4.08 g, 25.0 mmol) in dimethyl sulfoxide (38 mL), and the mixture was stirred at 25° C. for 5 min. To the mixture cyclopentyl bromide (37.5 mmol, 4.02 mL) was added, and the mixture stirred at 80° C. for 3 h. After cooling in ice, the mixture was poured into cold water and the resulting precipitate was collected by filtration in vacuo, washed with water (25 mL) and hexanes (15 mL) and dried in vacuo to afford 2-cyclopentyloxy-isoindole-1,3-dione (4.89 g, 85%) as an off-white solid which was used in the next step without further purification.

Hydrazine monohydrate (2.05 mL, 42.26 mmol) was added to a solution of 2-cyclopentyloxy-isoindole-1,3-dione (4.88 g, 21.10 mmol) in a mixture of methanol (2.67 mL) and methylene chloride (22 mL), and the mixture was stirred at 25° C. for 4 h. The resulting precipitate was filtered off in vacuo, and the filtrate was washed with 5.0 N aqueous ammonium hydroxide (11 mL). The aqueous layer was extracted with methylene chloride (2×25 mL). The combined organic layers were washed with brine, dried over magnesium sulfate and concentrated in vacuo to afford O-cyclopentyl-hydroxylamine (2.03 g, 95%) as a yellow oil: $H^1$-NMR (400 MHz, $CDCl_3$) δ=1.40-1.80 (8H, m), 4.10 (1H, m).

(3-Chloro-4-methanesulfonyl-phenyl)-oxo-acetic acid methyl ester (1.75 g, 6.32 mmol) was stirred in methanol (14 mL) and warmed in a 70° C. oil bath. O-Cyclopentyl-hydroxylamine (1.09 g, 7.92 mmol) was added. After 2 h, the reaction mixture was allowed to cool and concentrated in vacuo. Purification by flash column chromatography (Merck silica gel 60, 40-63 □m; 20% ethyl acetate/hexanes) gave (E)-(3-chloro-4-methanesulfonyl-phenyl)-cyclopentyloxyimino-acetic acid methyl ester (1.01 g, 44%) eluting second as a clear, colorless oil which solidified over time: $H^1$-NMR (400 MHz, $CDCl_3$) δ=1.62 (4H, m), 1.85 (4H, m), 3.31 (3H, s), 3.91 (3H, s), 4.96 (1H, m), 7.48 (1H, dd, J=8.2 Hz, J=1.3 Hz), 7.59 (1H, d, J=1.2 Hz), 8.17 (1H, d, J=8.2 Hz).

(E)-(3-Chloro-4-methanesulfonyl-phenyl)-cyclopentyloxyimino-acetic acid methyl ester (144 mg, 0.40 mmol) was dissolved in methanol (4 mL) and cooled in an ice bath. A 2.0 N solution of lithium hydroxide in water (0.60 mL, 1.2 mmol) was added dropwise. After stirring 1 h, the reaction mixture was diluted with chloroform (50 mL) and washed with 0.1 M aqueous potassium bisulfate (25 mL). The aqueous phase was extracted with chloroform (30 mL) and the combined organic phases were dried over magnesium sulfate and evaporated in vacuo to afford (E)-(3-chloro-4-methanesulfonyl-phenyl)-cyclopentyloxyimino-acetic acid which was used in the next step without further purification: $H^1$-NMR (400 MHz, $CDCl_3$) δ=1.65 (4H, m), 1.88 (4H, m), 3.31 (3H, s), 4.97 (1H, m), 7.58 (1H, dd, J=8.2 Hz, J=1.1 Hz), 7.67 (1H, d, J=1.1 Hz), 8.19 (1H, d, J=8.2 Hz).

(E)-(3-Chloro-4-methanesulfonyl-phenyl)-cyclopentyloxyimino-acetic acid (93 mg, 0.27 mmol), 1-methyl-1H-pyrazol-3-ylamine (29 µL, 0.30 mmol) and N,N-diisopropylethylamine (141 µL, 0.81 mmol) were combined in acetonitrile (1.25 mL) and cooled in an ice bath. O-(7-Azabenzotriazole-1-yl)-N,N,N'N'-tetramethyluronium hexafluorophosphate (103 mg, 0.27 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 60% ethyl acetate/hexanes) to afford (E)-2-(3-chloro-4-methanesulfonyl-phenyl)-2-cyclopentyloxyimino-N-(1-methyl-1H-pyrazol-3-yl)-acetamide (79 mg, 69%) as a white solid after lyophilization from aqueous acetonitrile: LC-MS (ESI) m/e calcd for $C_{18}H_{21}ClN_4O_4S$ [M+] 424.10, found 425 [M+H+]; H$^1$-NMR (400 MHz, CDCl$_3$) δ ppm 1.64 (m, 4 H, 2×CH$_2$), 1.86 (m, 4 H, 2×CH$_2$), 3.29 (s, 3 H, SO$_2$CH$_3$), 3.85 (s, 3 H, NCH$_3$), 4.88 (p, J=4.1 Hz, 1 H, OCH), 6.69 (d, J=2.3 Hz, 1 H, Ar), 7.28 (d, J=2.3 Hz, 1 H, Ar), 7.55 (dd, Jo=8.2, Jm=1.3 Hz, 1 H, Ar), 7.66 (d, Jm=1.3 Hz, 1 H, Ar), 8.18 (d, Jo=8.2 Hz, 1 H, Ar), 9.16 (s, 1 H, NH).

Example 2

(E)-2-(3-Chloro-4-methanesulfonyl-phenyl)-2-cyclopentyloxyimino-N-isoxazol-3-yl-acetamide

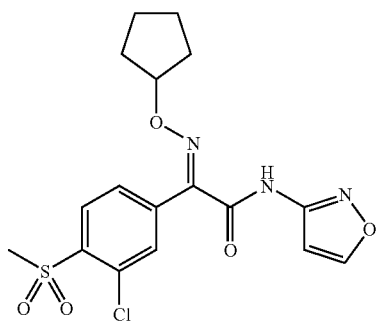

(E)-(3-Chloro-4-methanesulfonyl-phenyl)-cyclopentyloxyimino-acetic acid (prepared as in Example 1, 93 mg, 0.27 mmol), isoxazol-3-ylamine (29 µL, 0.30 mmol) and N,N-diisopropylethylamine (141 µL, 0.81 mmol) were combined in acetonitrile (1.25 mL) and cooled in an ice bath. O-(7-Azabenzotriazole-1-yl)-N,N,N'N'-tetramethyluronium hexafluorophosphate (103 mg, 0.27 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 25% ethyl acetate/hexanes) to afford (E)-2-(3-chloro-4-methanesulfonyl-phenyl)-2-cyclopentyloxyimino-N-isoxazol-3-yl-acetamide (37 mg, 33%) as a slightly yellow solid after lyophilization from aqueous acetonitrile: LC-MS (ESI) m/e calcd for $C_{17}H_{18}ClN_3O_5S$ [M+] 411.07, found 412 [M+H+]; H$^1$-NMR (400 MHz, CDCl$_3$) δ ppm 1.67 (m, 4 H, 2×CH$_2$), 1.88 (m, 4 H, 2×CH$_2$), 3.31 (s, 3 H, SO$_2$CH$_3$), 4.94 (m, 1 H, OCH), 7.07 (d, J=1.7 Hz, 1 H, Ar), 7.56 (dd, Jo=8.2, Jm=1.5 Hz, 1 H, Ar), 7.66 (d, Jm=1.5 Hz, 1 H, Ar), 8.20 (d, Jo=8.2 Hz, 1 H, Ar), 8.33 (d, J=1.7 Hz, 1 H, Ar), 9.40 (s, 1 H, NH).

Example 3

(E)-2-(3-Chloro-4-methanesulfonyl-phenyl)-2-cyclopentyloxyimino-N-thiazol-2-yl-acetamide

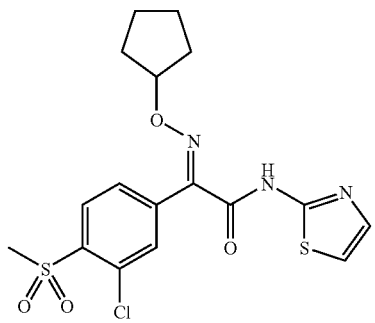

(E)-(3-Chloro-4-methanesulfonyl-phenyl)-cyclopentyloxyimino-acetic acid (prepared as in Example 1, 93 mg, 0.27 mmol), thiazol-2-ylamine (27 mg, 0.27 mmol) and N,N-diisopropylethylamine (141 µL, 0.82 mmol) were combined in acetonitrile (1.25 mL) and cooled in an ice bath. O-(7-Azabenzotriazole-1-yl)-N,N,N'N'-tetramethyluronium hexafluorophosphate (103 mg, 0.27 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 60% ethyl acetate/hexanes) to afford (E)-2-(3-chloro-4-methanesulfonyl-phenyl)-2-cyclopentyloxyimino-N-thiazol-2-yl-acetamide (71 mg, 62%) as a white solid after lyophilization from aqueous acetonitrile: LC-MS (ESI) m/e calcd for $C_{17}H_{18}ClN_3O_4S_2$ [M+] 427.04, found 428 [M+H+]; H$^1$-NMR (400 MHz, CDCl$_3$) δ ppm 1.68 (m, 4 H, 2×CH$_2$), 1.90 (m, 4 H, 2×CH$_2$), 3.32 (s, 3 H, SO$_2$CH$_3$), 4.96 (m, 1 H, OCH), 7.05 (d, J=3.5 Hz, 1 H, Ar), 7.52 (d, J=3.5 Hz, 1 H, Ar), 7.60 (dd, Jo=8.2, Jm=1.2 Hz, 1 H, Ar), 7.71 (d, Jm=1.2 Hz, 1 H, Ar), 8.20 (d, Jo=8.2 Hz, 1 H, Ar), 10.20 (s, 1 H, NH).

Example 4

(E)-2-(3-Chloro-4-methanesulfonyl-phenyl)-2-cyclopentyloxyimino-N-pyrazin-2-yl-acetamide

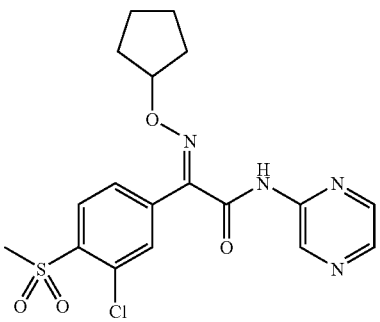

(E)-(3-Chloro-4-methanesulfonyl-phenyl)-cyclopentyloxyimino-acetic acid (prepared as in Example 1, 97 mg, 0.28 mmol), pyrazin-2-ylamine (29 mg, 0.31 mmol) and 4-methylmorpholine (123 μL, 1.12 mmol) were combined in N,N-dimethylformamide (1.5 mL) and cooled to 0° C. O-(7-Azabenzotriazole-1-yl)-N,N,N'N'-tetramethyluronium hexafluorophosphate (117 mg, 0.31 mmol) was added and the ice bath was removed. After stirring 16 h, further portions of pyrazin-2-ylamine (10 mg, 0.11 mmol), 4-methylmorpholine (41 μL, 0.37 mmol) and O-(7-azabenzotriazole-1-yl)-N,N,N'N'-tetramethyluronium hexafluorophosphate (39 mg, 0.10 mmol) were added. After stirring an additional 3 h, the reaction mixture was treated with ethyl acetate (100 mL) and saturated aqueous brine solution (200 mL). The phases were separated and the organic phase was washed with a 0.2 M aqueous potassium bisulfate solution and saturated aqueous brine solution (50 mL) and a 1:1 mixture of saturated aqueous sodium bicarbonate solution and saturated aqueous brine solution (50 mL) then dried over magnesium sulfate and evaporated in vacuo. The residue was purified by flash column chromatography (Merck silica gel 60, 40-63 μm; 50% ethyl acetate/hexanes) to afford (E)-2-(3-chloro-4-methanesulfonyl-phenyl)-2-cyclopentyloxyimino-N-pyrazin-2-yl-acetamide (62 mg, 52%) as a clear, colorless film which was then lyophilized from aqueous acetonitrile to afford a white solid: LC-MS (ESI) m/e calcd for $C_{18}H_{19}ClN_4O_4S$ [M$^+$] 422.08, found 423 [M+H$^+$]; H$^1$-NMR (400 MHz, CDCl$_3$) δ ppm 1.68 (m, 4 H, 2×CH$_2$), 1.91 (m, 4 H, 2×CH$_2$), 3.32 (s, 3 H, SO$_2$CH$_3$), 4.98 (m, 1 H, OCH), 7.57 (dd, Jo=8.2, Jm=1.5 Hz, 1 H, Ar), 7.68 (d, Jm=1.5 Hz, 1 H, Ar), 8.22 (d, Jo=8.2 Hz, 1 H, Ar), 8.33 (m, 1 H, Ar), 8.41 (m, 1 H, Ar), 9.29 (brs, 1 H, Ar), 9.56 (s, 1 H, NH).

Example 5

(E)-1-[2-(3-Chloro-4-methanesulfonyl-phenyl)-2-cyclopentyloxyimino-acetyl]-3-methyl-urea

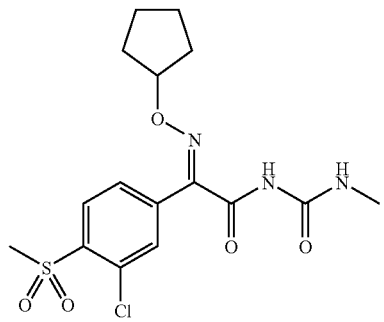

(E)-(3-Chloro-4-methanesulfonyl-phenyl)-cyclopentyloxyimino-acetic acid methyl ester (prepared as in Example 1, 98 mg, 0.27 mmol), methylurea (44 mg, 0.60 mmol) and a 6-10 wt. % solution of magnesium methoxide in methanol (1.33 mL, 0.10 mmol) were combined and warmed in a 70° C. oil bath for 16 h. After cooling, the reaction mixture was diluted with methanol (2 mL) and filtered through celite. The celite was washed with ethyl acetate (100 mL) and the combined filtrates were washed with water (40 mL), dried over magnesium sulfate and evaporated in vacuo. The residue was purified by flash column chromatography (Merck silica gel 60, 40-63 μm; 50% ethyl acetate/hexanes) to afford (E)-1-[2-(3-chloro-4-methanesulfonyl-phenyl)-2-cyclopentyloxy-imino-acetyl]-3-methyl-urea (40 mg, 36%) as a white solid after lyophilization from aqueous dioxane: LC-MS (ESI) m/e calcd for $C_{16}H_{20}ClN_3O_5S$ [M$^+$] 401.08, found 402 [M+H$^+$]; H$^1$-NMR (400 MHz, CDCl$_3$) δ ppm 1.65 (m, 4 H, 2×CH$_2$), 1.87 (m, 4 H, 2×CH$_2$), 2.94 (d, J=4.9 Hz, 3 H, NCH$_3$), 3.32 (s, 3 H, SO$_2$CH$_3$), 4.92 (m, 1 H, OCH), 7.50 (brd, Jo=8.2, 1 H, Ar), 7.60 (brs, 1 H, Ar), 8.02 (brm, 1 H, NH), 8.21 (d, Jo=8.2 Hz, 1 H, Ar), 8.82 (s, 1 H, NH).

Example 6

(E)-2-(3-Chloro-4-methanesulfonyl-phenyl)-2-isopropoxyimino-N-(1-methyl-1H-pyrazol-3-yl)-acetamide

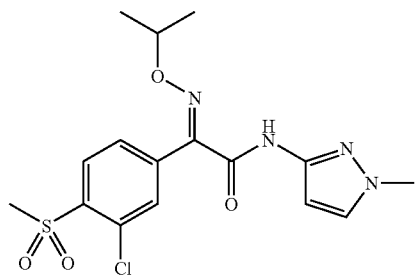

Solid potassium carbonate (8.64 g, 62.5 mmol) was added to a solution of N-hydroxyphthalimide (4.08 g, 25.0 mmol) in dimethyl sulfoxide (37 mL), and the mixture was stirred at 25° C. for 5 min. To the mixture, isopropyl bromide (3.41 mL, 37.5 mmol) was added, and the mixture stirred at 80° C. for 3 h. After ice-cooling, the mixture was poured into cold water and the resulting precipitate was collected by filtration in vacuo, washed with water (25 mL) and hexanes (15 mL) and dried in vacuo to afford 2-isopropyloxy-isoindole-1,3-dione (4.44 g, 86.6%) as a white solid which was used in the next step without further purification.

Hydrazine monohydrate (2.10 mL, 43.28 mmol) was added to a solution of 2-isopropyloxy-isoindole-1,3-dione (4.44 g, 21.64 mmol) in a mixture of methanol (11 mL) and methylene chloride (110 mL), and the mixture was stirred at 25° C. for 4 h. The resulting precipitate was filtered off in vacuo, and the filtrate was washed with 5.0 N aqueous ammonium hydroxide (11 mL). The aqueous layer was extracted with methylene chloride (2×25 mL). The combined organic layers were washed with brine, dried over magnesium sulfate and concentrated in vacuo. The residue was dissolved in a 4.0 M solution of hydrochloric acid in dioxane (12.5 mL) and diluted with diethyl ether (100 mL). The resulting precipitate was collected by filtration in vacuo to afford O-isopropyl-hydroxylamine hydrochloride (1.31 g, 54.3%) as a white solid, which was used in the next step without further purification.

(3-Chloro-4-methanesulfonyl-phenyl)-oxo-acetic acid methyl ester (prepared as in Example 1, 1.30 g, 4.70 mmol) was stirred in methanol (9.5 mL) and warmed in a 70° C. oil bath. O-Isopropyl-hydroxylamine hydrochloride (786 mg, 7.04 mmol) was added. After 7 h, the reaction mixture was allowed to cool and concentrated in vacuo. The residue was dissolved in ethyl acetate (100 mL) and washed with 0.2 M aqueous potassium bisulfate solution (50 mL), 50% aqueous sodium bicarbonate solution (50 mL) and brine (50 mL). The organic phase was dried over magnesium sulfate and concentrated in vacuo. Purification by flash column chromatography (Merck silica gel 60, 40-63 μm; 20% ethyl acetate/hexanes to 33% ethyl acetate/hexanes) afforded (E)-(3-chloro-4-methanesulfonyl-phenyl)-isopropoxyimino-acetic acid methyl ester as a faintly yellow oil contaminated with an unknown impurity (645 mg, <41%): LC-MS (ESI) m/e calcd for $C_{13}H_{16}ClNO_5S$ [M$^+$] 333.04, found 334 [M+H$^+$].

This estimated 80% pure (E)-(3-chloro-4-methanesulfonyl-phenyl)-isopropoxyimino-acetic acid methyl ester (0.52 g, <1.5 mmol) was dissolved in methanol (14 mL) and cooled to 0° C. An aqueous solution of lithium hydroxide (2.0 N, 1.86 mL, 3.72 mmol) was added dropwise. After stirring 1.25 h, the reaction mixture was diluted with chloroform (175 mL) and washed with 0.2 M aqueous potassium bisulfate solution (50 mL). The aqueous phase was extracted with chloroform (75 mL) and the combined organic phases were dried over magnesium sulfate and evaporated in vacuo to afford (E)-(3-chloro-4-methanesulfonyl-phenyl)-isopropoxyimino-acetic acid (506 mg, quant.) as a slightly yellow paste that was used without further purification.

This estimated 80% pure (E)-(3-chloro-4-methanesulfonyl-phenyl)-isopropoxyimino-acetic acid (130 mg, <0.39 mmol) was combined with N,N-diisopropylethylamine (162 µL, 0.93 mmol) and O-(7-azabenzotriazole-1-yl)-N,N,N'N'-tetramethyluronium hexafluorophosphate (118 mg, 0.31 mmol) in acetonitrile (1.5 mL) and cooled to 0° C. 1-Methyl-1H-pyrazol-3-ylamine (33 µL, 0.34 mmol) was added and the reaction mixture was allowed to warm to 25° C. and stirred overnight. After evaporating the volatiles under a stream of nitrogen, The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 60% ethyl acetate/hexanes) to afford (E)-2-(3-chloro-4-methanesulfonyl-phenyl)-2-isopropoxyimino-N-(1-methyl-1H-pyrazol-3-yl)-acetamide (56 mg, 45%) as a slightly yellow solid after lyophilization from aqueous dioxane: LC-MS (ESI) m/e calcd for $C_{16}H_{19}ClN_4O_4S$ [M$^+$] 398.08, found 399 [M+H$^+$]; H$^1$-NMR (400 MHz, CDCl$_3$) δ ppm 1.34 (d, J=6.3 Hz, 6 H, 2×CH$_3$), 3.30 (s, 3 H, SO$_2$CH$_3$), 3.86 (s, 3 H, NCH$_3$), 4.57 (m, J=6.3 Hz, 1 H, OCH), 6.70 (d, J=2.3 Hz, 1 H, Ar), 7.29 (d, J=2.3 Hz, 1 H, Ar), 7.58 (dd, Jo=8.2, Jm=1.5 Hz, 1 H, Ar), 7.69 (d, Jm=1.5 Hz, 1 H, Ar), 8.19 (d, Jo=8.2 Hz, 1 H, Ar), 9.14 (s, 1 H, NH).

Example 7

(E)-N-Benzothiazol-2-yl-2-(3-chloro-4-methanesulfonyl-phenyl)-2-isopropoxyimino-acetamide

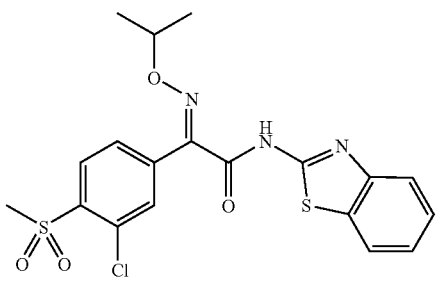

This estimated 80% pure (E)-(3-chloro-4-methanesulfonyl-phenyl)-isopropoxyimino-acetic acid (prepared as in Example 6, 99 mg, 0.31 mmol), 2-aminobenzothiazole (512 mg, 0.34 mmol) and N,N-diisopropylethylamine (162 µL, 0.93 mmol) were combined in acetonitrile (1.25 mL) and cooled in an ice bath. O-(7-Azabenzotriazole-1-yl)-N,N,N'N'-tetramethyluronium hexafluorophosphate (118 mg, 0.31 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 50% ethyl acetate/hexanes) to afford (E)-N-benzothiazol-2-yl-2-(3-chloro-4-methanesulfonyl-phenyl)-2-isopropoxyimino-acetamide (76 mg, 54%) as a white solid after lyophilization from aqueous acetonitrile: LC-MS (ESI) m/e calcd for $C_{19}H_{18}ClN_3O_4S_2$ [M$^+$] 451.04, found 452 [M+H$^+$]; H$^1$-NMR (400 MHz, CDCl$_3$) δ ppm 1.39 (d, J=6.3 Hz, 6 H, 2×CH$_3$), 3.32 (s, 3 H, SO$_2$CH$_3$), 4.65 (m, J=6.3 Hz, 1 H, OCH), 7.36 (brt, J=7.8 Hz, 1H, Ar), 7.49 (brt, J=7.8 Hz, 1H, Ar), 7.64 (dd, Jo=8.2, Jm=1.6 Hz, 1 H, Ar), 7.74 (d, Jm=1.6 Hz, 1 H, Ar), 7.84 (m, 2H, Ar), 8.24 (d, Jo=8.2 Hz, 1 H, Ar), 10.20 (s, 1 H, NH).

Example 8

(E)-2-(3-Chloro-4-methanesulfonyl-phenyl)-2-isopropoxyimino-N-(1H-pyrazol-3-yl)-acetamide

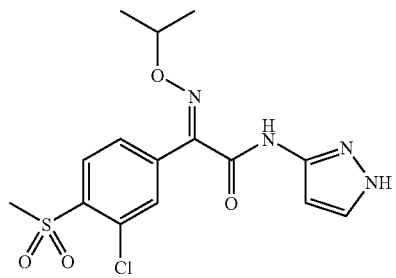

3-Amino-pyrazole (2 g, 24.1 mmol) was dissolved in 1,4-dioxane (60.25 mL) and triethylamine (6.77 mL, 48.2 mmol) was added followed by the dropwise addition of di-tert-butyl dicarbonate (5.78 g, 26.5 mmol). The solution stirred at 25° C. for 4 h. The mixture was concentrated in vacuo, diluted with ethyl acetate (100 mL), washed with water (2×50 mL), saturated aqueous brine solution (2×50 mL), dried over magnesium sulfate, filtered and concentrated in vacuo. Flash column chromatography (Merck silica gel 60, 40-63 µm; 20% ethyl acetate/hexanes to 50% ethyl acetate/hexanes) afforded 5-amino-pyrazole-1-carboxylic acid tert-butyl ester (less polar product, 2.53 g, 57.3%) as a white solid: H$^1$-NMR (400 MHz, CDCl$_3$) δ 1.656 (9H, s, 5.1-5.45 (2H, bs), 5.39 (1H, d, J=2 Hz), 7.37 (1H, d, J=2 Hz).

The estimated 80% pure (E)-(3-chloro-4-methanesulfonyl-phenyl)-isopropoxyimino-acetic acid and (prepared as in Example 6, 99 mg, 0.31 mmol), 5-amino-pyrazole-1-carboxylic acid tert-butyl ester (625 mg, 0.34 mmol) and N,N-diisopropylethylamine (162 µL, 0.93 mmol) were combined in acetonitrile (1.25 mL) and cooled in an ice bath. O-(7-Azabenzotriazole-1-yl)-N,N,N'N'-tetramethyluronium hexafluorophosphate (118 mg, 0.31 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 60% ethyl acetate/hexanes) to afford (E)-5-[2-(3-chloro-4-methanesulfonyl-phenyl)-2-isopropoxyimino-acetylamino]-pyrazole-1-carboxylic acid tert-butyl ester (30 mg, 20%) as a tan solid after lyophilization from aqueous acetonitrile: $H^1$-NMR (400 MHz, $CDCl_3$) δ=1.41 (6H, d, J=6.3 Hz), 1.72 (9H, s), 3.30 (3H, s), 4.66 (1H, m), 6.85 (1H, d, J=1.8 Hz), 7.60 (2H, m), 7.70 (1H, d, J=1.5 Hz), 8.20 (1H, d, J=8.0 Hz), 11.64 (1H, s).

(E)-5-[2-(3-Chloro-4-methanesulfonyl-phenyl)-2-isopropoxyimino-acetylamino]-pyrazole-1-carboxylic acid tert-butyl ester (30 mg, 0.06 mmol) was dissolved in dioxane (1 mL). A 4.0 M solution of hydrochloric acid in dioxane (1 mL, 4 mmol) was added. After stirring 1 h, the volatiles were evaporated in vacuo and the residue was diluted with chloroform (3 mL) and washed with 10% aqueous potassium carbonate solution (1 mL). The aqueous phase was extracted with chloroform (2 mL) and the combined organic phases were filtered through sodium sulfate and evaporated in vacuo. The residue was purified by flash column chromatography (Merck silica gel 60, 40-63 μm; 2% methanol/chloroform) to afford (E)-2-(3-chloro-4-methanesulfonyl-phenyl)-2-isopropoxyimino-N-(1H-pyrazol-3-yl)-acetamide (14 mg, 59%) as a white solid after lyophilization from aqueous dioxane: LC-MS (ESI) m/e calcd for $C_{15}H_{17}ClN_4O_4S$ [$M^+$] 384.07, found 385 [$M+H^+$]; $H^1$-NMR (400 MHz, $CDCl_3$) δ ppm 1.35 (d, J=6.3 Hz, 6 H, 2×$CH_3$), 3.32 (s, 3 H, $SO_2CH_3$), 4.60 (m, J=6.3 Hz, 1 H, OCH), 6.77 (brs, 1H, Ar), 7.53 (d, J=2.3 Hz, 1 H, Ar), 7.58 (dd, Jo=8.2, Jm=1.5 Hz, 1 H, Ar), 7.68 (d, Jm=1.5 Hz, 1 H, Ar), 8.20 (d, Jo=8.2 Hz, 1 H, Ar), 9.25 (s, 1 H, NH).

Example 9

(E)-2-(3-Chloro-4-methanesulfonyl-phenyl)-2-cyclohexyloxyimino-N-(1-methyl-1H-pyrazol-3-yl)-acetamide

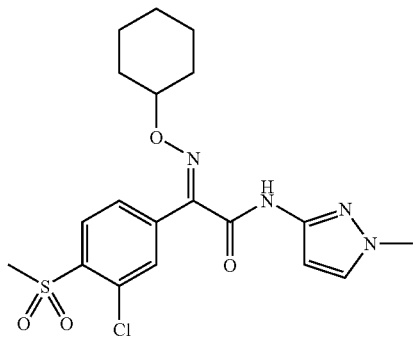

Solid potassium carbonate (6.91 g, 50.0 mmol) was added to a solution of N-hydroxyphthalimide (4.08 g, 25.0 mmol) and 18-crown-6 (661 mg, 2.5 mmol) in dimethyl sulfoxide (62 mL), and the mixture was stirred at 25° C. for 5 min. To the mixture cyclohexyl bromide (12.3 mL, 100.0 mmol) was added, and the mixture stirred at 80° C. for 3 h. After ice-cooling, the mixture was poured into cold water and the resulting precipitate was collected by filtration in vacuo, washed with water (25 mL) and hexanes (15 mL) and dried in vacuo to afford 2-cyclohexyloxy-isoindole-1,3-dione (5.67 g, 93%) as a white solid which was used in the next step without further purification.

Hydrazine monohydrate (2.24 mL, 42.20 mmol) was added to a solution of 2-cyclohexyloxy-isoindole-1,3-dione (4.88 g, 21.10 mmol) in a mixture of methanol (12 mL) and methylene chloride (120 mL), and the mixture was stirred at 25° C. for 4 h. The resulting precipitate was filtered off in vacuo, and the filtrate was washed with 5.0 N aqueous ammonium hydroxide (60 mL). The aqueous layer was extracted with methylene chloride (2×25 mL). The combined organic layers were washed with brine, dried over magnesium sulfate and concentrated in vacuo. The residue was dissolved in a 4.0 M solution of hydrochloric acid in dioxane (12 mL) and diluted with diethyl ether (70 mL). The resulting precipitate was collected by filtration in vacuo to afford O-cyclohexyl-hydroxylamine hydrochloride (1.71 g, 45.7%) as a white solid, which was used in the next step without further purification.

(3-Chloro-4-methanesulfonyl-phenyl)-oxo-acetic acid methyl ester (prepared as in Example 1, 1.2 g, 4.34 mmol) was stirred in methanol (9 mL) and warmed in a 70° C. oil bath. O-Cyclohexyl-hydroxylamine hydrochloride (0.811 g, 5.43 mmol) was added. After 2 h, the reaction mixture was allowed to cool and concentrated in vacuo. Purification by flash column chromatography (Merck silica gel 60, 40-63 μm; 20% ethyl acetate/hexanes to 50% ethyl acetate/hexanes) afforded (E)-(3-chloro-4-methanesulfonyl-phenyl)-cyclohexyloxyimino-acetic acid methyl ester as a white solid (552 mg, 34%): $H^1$-NMR (400 MHz, $CDCl_3$) δ=1.34 (3H, m), 1.51 (3H, m), 1.68 (2H, m), 1.96 (2H, m), 3.31 (3H, s), 3.91 (3H, s), 4.39 (1H, m), 7.51 (1H, dd, J=8.1 Hz, J=1.5 Hz), 7.62 (1H, d, J=1.5 Hz), 8.18 (1H, d, J=8.1 Hz).

(E)-(3-Chloro-4-methanesulfonyl-phenyl)-cyclohexyloxyimino-acetic acid methyl ester (487 mg, 1.30 mmol) was dissolved in methanol (14 mL) and cooled to 0° C. A 2.0 N aqueous solution of lithium hydroxide (1.95 mL, 3.90 mmol) was added dropwise and the cooling bath was removed. After stirring 1 h, the reaction mixture was diluted with chloroform (175 mL) and washed with 0.2 M aqueous potassium bisulfate solution (50 mL). The aqueous phase was extracted with chloroform (75 mL) and the combined organic phases were dried over magnesium sulfate and evaporated in vacuo to afford (E)-(3-chloro-4-methanesulfonyl-phenyl)-cyclohexyloxyimino-acetic acid (458 mg, 98%) as a white foam that was used without further purification.

(E)-(3-chloro-4-methanesulfonyl-phenyl)-cyclohexyloxyimino-acetic acid (112 mg, 0.31 mmol), N,N-diisopropylethylamine (163 μL, 0.94 mmol) and 1-methyl-1H-pyrazol-3-ylamine (30 μL, 0.31 mmol) were combined in methylene chloride (1.5 mL) and cooled to 0° C. O-(7-Azabenzotriazole-1-yl)-N,N,N'N'-tetramethyluronium hexafluorophosphate (118 mg, 0.31 mmol) was added and the cooling bath was removed. After stirring 16 h, the reaction mixture was diluted with chloroform (2 mL) and washed with saturated aqueous sodium bicarbonate solution (1.5 mL). The aqueous phase was extracted with chloroform (1.5 mL) and the combined organic phases were filtered through sodium sulfate and evaporated in vacuo. The residue was purified by flash column chromatography (Merck silica gel 60, 40-63 μm; 50% ethyl acetate/hexanes) to afford (E)-2-(3-chloro-4-methanesulfonyl-phenyl)-2-cyclohexyloxyimino-N-(1-methyl-1H-pyrazol-3-yl)-acetamide (110 mg, 81%) as a white solid after lyophilization from aqueous dioxane: LC-MS (ESI) m/e calcd for $C_{19}H_{23}ClN_4O_4S$ [$M^+$] 438.11, found 439 [$M+H^+$]; $H^1$-NMR (400 MHz, $CDCl_3$) δ ppm 1.24-1.61 (m, 6H, 3×$CH_2$), 1.71 (m, 2H, 2×CH of $CH_2$), 1.96 (m, 2H, 2×CH of $CH_2$), 3.29 (s, 3 H, $SO_2CH_3$), 3.85 (s, 3 H, $NCH_3$), 4.29 (m, 1 H, OCH), 6.69 (d, J=2.3 Hz, 1 H, Ar), 7.28 (d, J=2.3 Hz, 1 H, Ar), 7.60 (dd, Jo=8.2, Jm=1.5 Hz, 1 H, Ar), 7.71 (d, Jm=1.5 Hz, 1 H, Ar), 8.20 (d, Jo=8.2 Hz, 1 H, Ar), 9.15 (s, 1 H, NH).

Example 10

(E)-2-(3-Chloro-4-methanesulfonyl-phenyl)-2-cyclohexyloxyimino-N-(3-methyl-[1,2,4]thiadiazol-5-yl)-acetamide

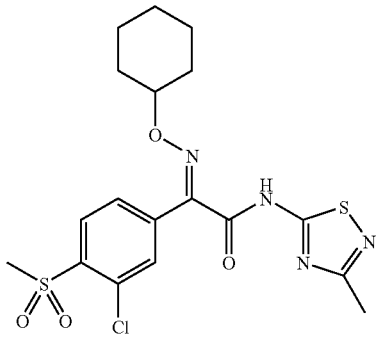

(E)-(3-Chloro-4-methanesulfonyl-phenyl)-cyclohexyloxyimino-acetic acid (prepared as in Example 9, 112 mg, 0.31 mmol), 3-methyl-[1,2,4]thiadiazol-5-ylamine (36 mg, 0.31 mmol) and N,N-diisopropylethylamine (163 μL, 0.93 mmol) were combined in acetonitrile (1.25 mL) and cooled in an ice bath. O-(7-Azabenzotriazole-1-yl)-N,N,N'N'-tetramethyluronium hexafluorophosphate (118 mg, 0.31 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 40% ethyl acetate/hexanes) to afford (E)-2-(3-chloro-4-methanesulfonyl-phenyl)-2-cyclohexyloxyimino-N-(3-methyl-[1,2,4]thiadiazol-5-yl)-acetamide (57 mg, 40%) as a white solid after lyophilization from aqueous acetonitrile: LC-MS (ESI) m/e calcd for $C_{18}H_{21}ClN_4O_4S_2$ [M$^+$] 456.07, found 457 [M+H$^+$]; H$^1$-NMR (400 MHz, CDCl$_3$) δ ppm 1.25-1.64 (m, 6H, 3×CH$_2$), 1.73 (m, 2H, 2×CH of CH$_2$), 2.00 (m, 2H, 2×CH of CH$_2$), 2.60 (s, 3 H, ArCH$_3$), 3.31 (s, 3 H, SO$_2$CH$_3$), 4.37 (m, 1 H, OCH), 7.64 (dd, Jo=8.2, Jm=1.5 Hz, 1 H, Ar), 7.74 (d, Jm=1.5 Hz, 1 H, Ar), 8.23 (d, Jo=8.2 Hz, 1 H, Ar), 10.35 (s, 1 H, NH).

Example 11

(E)-N-Benzothiazol-2-yl-2-(3-chloro-4-methanesulfonyl-phenyl)-2-cyclohexyloxyimino-acetamide

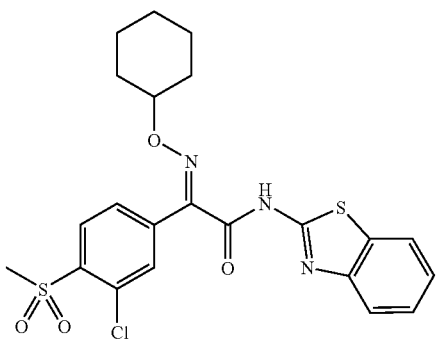

(E)-(3-Chloro-4-methanesulfonyl-phenyl)-cyclohexyloxyimino-acetic acid (prepared as in Example 9, 112 mg, 0.31 mmol), 2-aminobenzothiazole (47 mg, 0.31 mmol) and N,N-diisopropylethylamine (163 μL, 0.93 mmol) were combined in acetonitrile (1.25 mL) and cooled in an ice bath. O-(7-Azabenzotriazole-1-yl)-N,N,N'N'-tetramethyluronium hexafluorophosphate (118 mg, 0.31 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 60% ethyl acetate/hexanes) to afford (E)-N-benzothiazol-2-yl-2-(3-chloro-4-methanesulfonyl-phenyl)-2-cyclohexyloxyimino-acetamide (86 mg, 56%) as a white solid after lyophilization from aqueous acetonitrile: LC-MS (ESI) m/e calcd for $C_{22}H_{22}ClN_3O_4S_2$ [M$^+$] 491.07, found 492 [M+H$^+$]; H$^1$-NMR (400 MHz, CDCl$_3$) δ ppm 1.26-1.64 (m, 6H, 3×CH$_2$), 1.75 (m, 2H, 2×CH of CH$_2$), 2.00 (m, 2H, 2×CH of CH$_2$), 3.32 (s, 3 H, SO$_2$CH$_3$), 4.36 (m, 1 H, OCH), 7.35 (brt, 1 H, Ar), 7.48 (brt, 1 H, Ar), 7.65 (dd, Jo=8.2, Jm=1.5 Hz, 1 H, Ar), 7.76 (d, Jm=1.5 Hz, 1 H, Ar), 7.83 (brt, 2H, Ar), 8.23 (d, Jo=8.2 Hz, 1 H, Ar), 10.24 (s, 1 H, NH).

Example 12

(E)-2-[2-(3-Chloro-4-methanesulfonyl-phenyl)-2-cyclohexyloxyimino-acetylamino]-thiazole-5-carboxylic acid amide

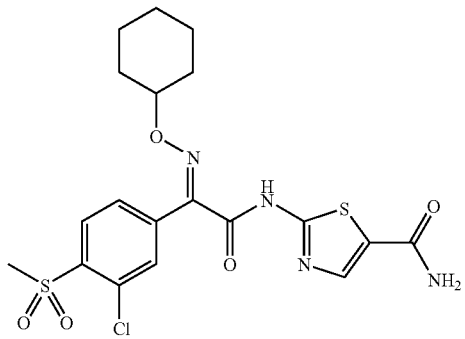

2-Amino-thiazole-5-carboxylic acid methyl ester (333 mg, 2.11 mmol) and a solution of concentrated ammonium hydroxide (4.2 mL) were combined and heated to 50° C. After stirring 72 h, the mixture was cooled, filtered and the filtrate was concentrated in vacuo to half the original volume. The precipitate was collected by filtration in vacuo and washed with water. Drying in vacuo afforded the desired product, 2-amino-thiazole-5-carboxylic acid amide (148 mg, 49%) as a tan solid that was used without further purification: LC-MS (ESI) m/e calcd for $C_4H_5N_3OS$ [M$^+$] 103.02, found 286.9 [2M+H$^+$]; H$^1$-NMR (400 MHz, CD$_3$OD) δ=7.59 (1H, s).

(E)-(3-chloro-4-methanesulfonyl-phenyl)-cyclohexyloxyimino-acetic acid (prepared as in Example 9, 112 mg, 0.31 mmol), N,N-diisopropylethylamine (163 μL, 0.94 mmol) and 2-amino-thiazole-5-carboxylic acid amide (54 mg, 0.38 mmol) were combined in methylene chloride (1.5 mL) and cooled to 0° C. O-(7-Azabenzotriazole-1-yl)-N,N,N'N'-tetramethyluronium hexafluorophosphate (118 mg, 0.31 mmol) was added and the cooling bath was removed. After stirring 16 h, thin layer chromatography analysis showed no reaction. N,N-dimethylformamide (1 mL) was added and the methylene chloride was removed in vacuo. The reaction mixture was stirred 20 h more then concentrated in vacuo and purified by flash column chromatography (Merck silica gel 60, 40-63 μm; 2% methanol/chloroform) to afford (E)-2-[2-(3-chloro-4-methanesulfonyl-phenyl)-2-cyclohexyloxyimino-acetylamino]-thiazole-5-carboxylic acid amide (33 mg, 22%) as a white solid after lyophilization from aqueous dioxane: LC-MS (ESI) m/e calcd for $C_{19}H_{21}ClN_4O_5S_2$ [M+] 484.06, found 485 [M+H+]; $H^1$-NMR (400 MHz, CDCl$_3$) δ ppm 1.26-1.79 (m, 8H, 4×CH$_2$), 2.00 (m, 2H, 2×CH of CH$_2$), 3.32 (s, 3 H, SO$_2$CH$_3$), 4.40 (m, 1 H, OCH), 5.82 (brs, 2 H, NH$_2$), 7.64 (dd, Jo=8.2, Jm=1.5 Hz, 1 H, Ar), 7.74 (d, Jm=1.5 Hz, 1 H, Ar), 7.96 (s, 1H, Ar), 8.23 (d, Jo=8.2 Hz, 1 H, Ar), 10.23 (s, 1 H, NH).

Example 13

(E)-2-(3-Chloro-4-methanesulfonyl-phenyl)-2-cyclopentyloxyimino-N-(3-methyl-[1,2,4]thiadiazol-5-yl)-acetamide

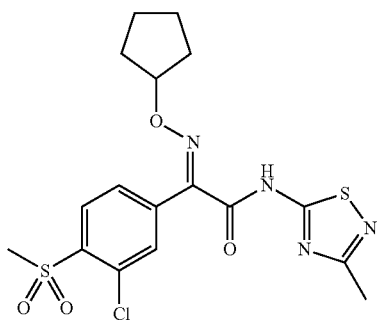

(E)-(3-Chloro-4-methanesulfonyl-phenyl)-cyclopentyloxyimino-acetic (prepared as in Example 1, 96 mg, 0.28 mmol), 3-methyl-[1,2,4]thiadiazol-5-ylamine (32 mg, 0.28 mmol) and N,N-diisopropylethylamine (145 μL, 0.83 mmol) were combined in acetonitrile (1.25 mL) and cooled in an ice bath. O-(7-Azabenzotriazole-1-yl)-N,N,N'N'-tetramethyluronium hexafluorophosphate (106 mg, 0.28 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 40% ethyl acetate/hexanes) to afford (E)-2-(3-chloro-4-methanesulfonyl-phenyl)-2-cyclopentyloxyimino-N-(3-methyl-[1,2,4]thiadiazol-5-yl)-acetamide (62 mg, 50%) as a white solid after lyophilization from aqueous acetonitrile: LC-MS (ESI) m/e calcd for $C_{17}H_{19}ClN_4O_4S_2$ [M+] 442.05, found 443 [M+H+]; $H^1$-NMR (400 MHz, CDCl$_3$) δ ppm 1.67 (m, 4 H, 2×CH$_2$), 1.90 (m, 4 H, 2×CH$_2$), 2.60 (s, 3 H, ArCH$_3$), 3.32 (s, 3 H, SO$_2$CH$_3$), 4.95 (m, 1 H, OCH), 7.60 (dd, Jo=8.3, Jm=1.6 Hz, 1 H, Ar), 7.70 (d, Jm=1.6 Hz, 1 H, Ar), 8.22 (d, Jo=8.3 Hz, 1 H, Ar), 10.35 (s, 1 H, NH).

Example 14

(E)-N-Benzothiazol-2-yl-2-(3-chloro-4-methanesulfonyl-phenyl)-2-cyclopentyloxyimino-acetamide

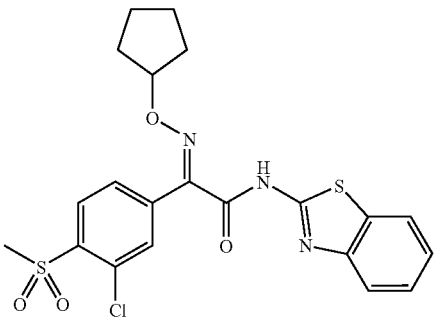

(E)-(3-Chloro-4-methanesulfonyl-phenyl)-cyclopentyloxyimino-acetic acid (prepared as in Example 1, 96 mg, 0.28 mmol), 2-aminobenzothiazole (42 mg, 0.28 mmol) and N,N-diisopropylethylamine (145 μL, 0.83 mmol) were combined in acetonitrile (1.25 mL) and cooled in an ice bath. O-(7-Azabenzotriazole-1-yl)-N,N,N'N'-tetramethyluronium hexafluorophosphate (106 mg, 0.28 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 40% ethyl acetate/hexanes) to afford (E)-N-benzothiazol-2-yl-2-(3-chloro-4-methanesulfonyl-phenyl)-2-cyclopentyloxyimino-acetamide (93 mg, 70%) as a white solid after lyophilization from aqueous acetonitrile: LC-MS (ESI) m/e calcd for $C_{21}H_{20}ClN_3O_4S_2$ [M+] 477.06, found 478 [M+H+]; $H^1$-NMR (400 MHz, CDCl$_3$) δ ppm 1.68 (m, 4 H, 2×CH$_2$), 1.90 (m, 4 H, 2×CH$_2$), 3.32 (s, 3 H, SO$_2$CH$_3$), 4.96 (m, 1 H, OCH), 7.35 (ddd, Jo=7.9, Jo=7.3, Jm=1.2 Hz, 1 H, Ar), 7.48 (ddd, Jo=8.2, Jo=7.3, Jm=1.2 Hz, 1 H, Ar), 7.61 (dd, Jo=8.2, Jm=1.6 Hz, 1 H, Ar), 7.72 (d, Jm=1.6 Hz, 1 H, Ar), 7.84 (m, 2H, Ar), 8.23 (d, Jo=8.2 Hz, 1 H, Ar), 10.21 (s, 1 H, NH).

Example 15

(E)-4-{3-[2-(3-Chloro-4-methanesulfonyl-phenyl)-2-cyclopentyloxyimino-acetylamino]-pyrazol-1-ylmethyl}-benzoic acid methyl ester

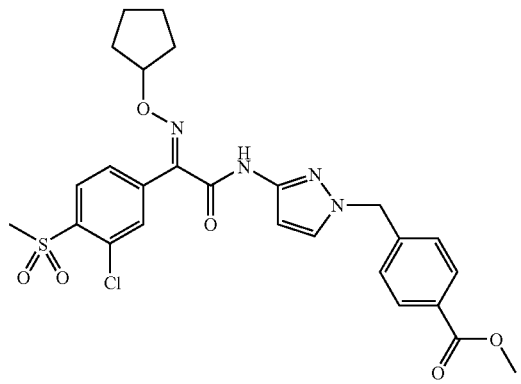

A solution of 1-nitro-1H-pyrazole (4.00 g, 35.4 mmol) in 40 mL of benzonitrile was refluxed for 2 h. After being cooled to 25° C., the mixture was poured into hexanes (160 mL). A white solid precipitated which was filtered and dried in vacuo, to afford 3-Nitro-1H-pyrazole (3.16 g, 79%): $H^1$-NMR (400 MHz, DMSO-$d_6$) δ7.01 (1H, d, J=2.4 Hz), 8.01 (d, 1H, J=3.4 Hz).

3-Nitro-1H-pyrazole (1.1 8 g, 10.44 mmol) was dissolved in anhydrous N,N-dimethylformamide (15 mL) and a 60% suspension of sodium hydride in mineral oil (500 mg, 12.53 mmol) was added while stirring under nitrogen. After the effervescence ceased and the mixture stirred for an additional 25 min, the mixture was chilled to 0° C. and the 4-bromomethyl-benzoic acid methyl ester (2.63 g, 11.48 mmol) was added. The mixture continued to stir under nitrogen at 0° C. for 20 min. The solution was poured into ice water, a white precipitate formed and was collected by vacuum filtration and dried in vacuo for 16 h. Recrystallization from hexanes and ethyl acetate (~4:1) gave the desired product, 4-(3-nitro-pyrazol-1-ylmethyl)-benzoic acid methyl ester (1.2 g, 44% yield), as a white powder upon collection and drying in vacuo: $H^1$-NMR (400 MHz, CDCl$_3$) δ=3.93 (3H, s), 5.43 (2H, s), 6.93 (1H, d, J=2.4 Hz), 7.33 (2H, d, J=8.4 Hz), 7.42 (1H, d, J=2.8 Hz), 8.05 (2H, d, J=8.4 Hz).

The 4-(3-nitro-pyrazol-1-ylmethyl)-benzoic acid methyl ester (1.2 g, 4.59 mmol) was dissolved in ethyl acetate (10 mL) and methanol (10 mL) was added. While stirring, a 50% slurry of raney nickel in water (1 mL) was added followed by hydrazine (1 mL). Immediate effervescence was observed. The mixture continued to stir and bubble for 30 min. The mixture was passed through a plug of celite and concentrated in vacuo to afford a yellow oil. The oil was taken up in ethyl acetate (100 mL), washed with water (2×20 mL), saturated aqueous brine solution (20 mL), dried over magnesium sulfate and concentrated in vacuo to afford the desired product 4-(3-amino-pyrazol-1-ylmethyl)-benzoic acid methyl ester (580 mg, 55% yield) as a beige powder: LC-MS (ESI) m/e calcd for $C_{12}H_{13}N_3O_2$ [$M^+$] 231.10, found 232 [$M+H^+$].

(E)-(3-chloro-4-methanesulfonyl-phenyl)-cyclopentyloxyimino-acetic acid (prepared as in Example 1, 157 mg, 0.45 mmol), 4-(3-amino-pyrazol-1-ylmethyl)-benzoic acid methyl ester (117 mg, 0.50 mmol) and N,N-diisopropylethylamine (237 μL, 1.36 mmol) were combined in methylene chloride (20 mL) and cooled in an ice bath. O-(7-Azabenzotriazole-1-yl)-N,N,N'N'-tetramethyluronium hexafluorophosphate (173 mg, 0.45 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 50% ethyl acetate/hexanes) to afford (E)-4-{3-[2-(3-chloro-4-methanesulfonyl-phenyl)-2-cyclopentyloxyimino-acetylamino]-pyrazol-1-ylmethyl}-benzoic acid methyl ester (188 mg, 74%) as a white solid after lyophilization from aqueous acetonitrile: LC-MS (ESI) m/e calcd for $C_{26}H_{27}ClN_4O_6S$ [$M^+$] 558.13, found 559 [$M+H^+$]; $H^1$-NMR (400 MHz, CDCl$_3$) δ ppm 1.63 (m, 4 H, 2×CH$_2$), 1.85 (m, 4 H, 2×CH$_2$), 3.29 (s, 3 H, SO$_2$CH$_3$), 3.92 (s, 3 H, CO$_2$CH$_3$), 4.86 (m, 1 H, OCH), 5.29 (s, 2H, NCH$_2$), 6.79 (d, J=2.3 Hz, 1 H, Ar), 7.23 (d, J=8.3 Hz, 2 H, Ar), 7.40 (d, J=2.3 Hz, 1 H, Ar), 7.55 (dd, Jo=8.2, Jm=1.5 Hz, 1 H, Ar), 7.65 (d, Jm=1.5 Hz, 1 H, Ar), 8.02 (d, J=8.3 Hz, 2 H, Ar), 8.18 (d, Jo=8.2 Hz, 1 H, Ar), 9.20 (s, 1 H, NH).

Example 16

(E)-2-[2-(3-Chloro-4-methanesulfonyl-phenyl)-2-cyclopentyloxyimino-acetylamino]-thiazole-5-carboxylic acid amide

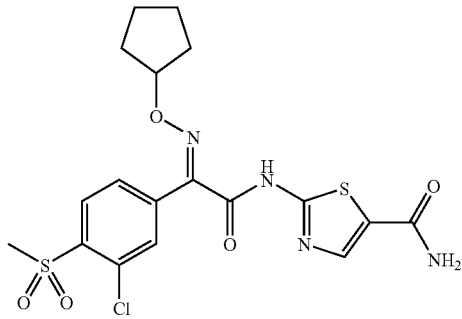

(E)-(3-Chloro-4-methanesulfonyl-phenyl)-cyclopentyloxyimino-acetic acid (prepared as in Example 1, 96 mg, 0.28 mmol), N,N-diisopropylethylamine (145 μL, 0.83 mmol) and 2-amino-thiazole-5-carboxylic acid amide (prepared as in Example 12, 48 mg, 0.34 mmol) were combined in acetonitrile (1.4 mL) and cooled to 0° C. O-(7-Azabenzotriazole-1-yl)-N,N,N'N'-tetramethyluronium hexafluorophosphate (106 mg, 0.28 mmol) was added and the cooling bath was removed. After stirring 16 h, the reaction mixture was treated with saturated aqueous sodium bicarbonate solution (30 mL) and extracted with 10% methanol/chloroform (3×35 mL). The combined organic phases were dried over magnesium sulfate and evaporated in vacuo. The residue was purified by flash column chromatography (Merck silica gel 60, 40-63 μm; 2% methanol/chloroform) to afford (E)-2-[2-(3-chloro-4-methanesulfonyl-phenyl)-2-cyclopentyloxyimino-acetylamino]-thiazole-5-carboxylic acid amide (16 mg, 12%) as a white solid after lyophilization from aqueous dioxane: LC-MS (ESI) m/e calcd for $C_{18}H_{19}ClN_4O_5S_2$ [$M^+$] 470.05, found 471 [$M+H^+$]: $H^1$-NMR (400 MHz, CD$_3$OD) δ ppm 1.66 (m, 4 H, 2×CH$_2$), 1.92 (m, 4 H, 2×CH$_2$), 3.34 (s, 3 H, SO$_2$CH$_3$), 5.04 (m, 1 H, OCH), 7.66 (dd, Jo=8.2, Jm=1.6 Hz, 1 H, Ar), 7.78 (d, Jm=1.6 Hz, 1 H, Ar), 8.05 (s, 1H, Ar), 8.17 (d, Jo=8.2 Hz, 1 H, Ar).

Example 17

(E)-4-{3-[2-(3-Chloro-4-methanesulfonyl-phenyl)-2-cyclopentyloxyimino-acetylamino]-pyrazol-1-ylmethyl}-benzamide

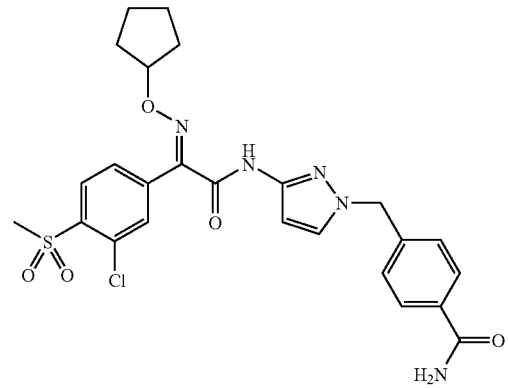

(E)-4-{3-[2-(3-Chloro-4-methanesulfonyl-phenyl)-2-cyclopentyloxyimino-acetylamino]-pyrazol-1-ylmethyl}-benzoic acid methyl ester (prepared as in Example 15, 134 mg, 0.24 mmol) was stirred in methanol (2.4 mL) and cooled to 0° C. A 2.0 N solution of lithium hydroxide in water (360 µL, 0.72 mmol) was added dropwise and the cooling bath was removed. After stirring 1.5 h, tetrahydrofuran (1 mL) was added to afford a more homogenous mixture. After stirring 60 h more, the volatiles were removed in vacuo and the residue was treated with 0.3 M aqueous potassium bisulfate solution (30 mL) and extracted with methylene chloride (3×30 mL). The combined organic phases were dried over magnesium sulfate and evaporated in vacuo to afford the crude intermediate carboxylic acid, which was used without further purification. This intermediate was stirred in methylene chloride (0.8 mL). One drop of N,N-dimethylformamide and a solution of a 2.0 M solution of oxalyl chloride in methylene chloride (80 µL, 1.6 mmol) were added. After stirring 1 h, the volatiles were evaporated in vacuo to afford the crude carboxylic acid chloride, which was used without further purification. This intermediate was dissolved in methylene chloride (2 mL) and concentrated ammonium hydroxide (30 µL) was added. After stirring 2 h more, the reaction mixture was treated with water (25 mL) and extracted with 10% methanol/chloroform (3×35 mL). The combined organic phases were dried over magnesium sulfate and evaporated in vacuo. The residue was purified by flash column chromatography (Merck silica gel 60, 40-63 µm; 2% methanol/chloroform) to afford (E)-4-{3-[2-(3-chloro-4-methanesulfonyl-phenyl)-2-cyclopentyloxyimino-acetylamino]-pyrazol-1-ylmethyl}-benzamide (39 mg, 30%) after lyophilization from aqueous dioxane: LC-MS (ESI) m/e calcd for $C_{25}H_{26}ClN_5O_5S$ [M$^+$] 543.13, found 544 [M+H$^+$]; H$^1$-NMR (400 MHz, CDCl$_3$) □ ppm 1.63 (m, 4 H, 2×CH$_2$), 1.84 (m, 4 H, 2×CH$_2$), 3.29 (s, 3 H, SO$_2$CH$_3$), 4.86 (m, 1 H, OCH), 5.28 (s, 2H, NCH$_2$), 5.82 (brs, 1 H, NH of NH$_2$), 6.08 (brs, 1 H, NH of NH$_2$), 6.79 (d, J=2.3 Hz, 1 H, Ar), 7.25 (d, J=8.3 Hz, 2 H, Ar), 7.40 (d, J=2.3 Hz, 1 H, Ar), 7.54 (dd, Jo=8.2, Jm=1.5 Hz, 1 H, Ar), 7.64 (d, Jm=1.5 Hz, 1 H, Ar), 7.80 (d, J=8.3 Hz, 2 H, Ar), 8.17 (d, Jo=8.2 Hz, 1 H, Ar), 9.20 (s, 1 H, NH).

Example 18

(E)-2-Cyclopentyloxyimino-2-(3,4-dichloro-phenyl)-N-(1-methyl-1H-pyrazol-3-yl)-acetamide

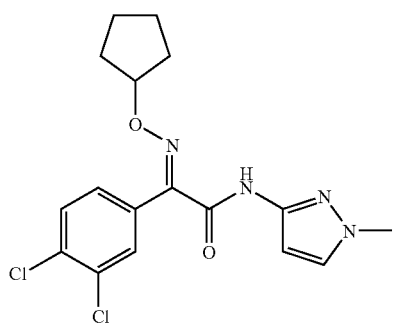

(3,4-Dichloro-phenyl)-oxo-acetic acid ethyl ester (1.08 g, 4.37 mmol) was stirred in ethanol (9.7 mL) and warmed in a 70° C. oil bath. O-Cyclopentyl-hydroxylamine (prepared as in Example 1, 722 mg, 5.25 mmol) was added. After 2 h, the reaction mixture was allowed to cool and concentrated in vacuo. Purification by flash column chromatography (Merck silica gel 60, 40-63 µm; 33% methylene chloride/hexanes) afforded (E)-cyclopentyloxyimino-(3,4-dichloro-phenyl)-acetic acid ethyl ester (371 mg, 26%) as a clear, colorless oil: H$^1$-NMR (400 MHz, CDCl$_3$) δ=1.37 (3H, t, J=7.1 Hz), 1.63 (4H, m), 1.85 (4H, m), 4.36 (2H, q, J=7.1 Hz), 4.94 (1H, m), 7.26 (1H, dd, J=8.3 Hz, J=1.9 Hz), 7.46 (1H, d, J=8.3 Hz), 7.54 (1H, d, J=1.9 Hz).

(E)-Cyclopentyloxyimino-(3,4-dichloro-phenyl)-acetic acid ethyl ester (332 mg, 1.01 mmol) was dissolved in ethanol (10 mL) and cooled to 0° C. A 2.0 N solution of lithium hydroxide in water (1.51 mL, 3.02 mmol) was added dropwise. The reaction mixture was allowed to gradually warm to 25° C. over 1.5 h, then diluted with chloroform (125 mL) and washed with 0.3 M potassium bisulfate solution (60 mL). The aqueous phase was extracted with chloroform (75 mL) and the combined organic phases were dried over magnesium sulfate and evaporated in vacuo to afford (E)-cyclopentyloxyimino-(3,4-dichloro-phenyl)-acetic acid as a faintly yellow semi-solid (304 mg, quant.) that was used without further purification.

(E)-Cyclopentyloxyimino-(3,4-dichloro-phenyl)-acetic acid (100 mg, 0.33 mmol) was dissolved in methylene chloride (1.6 mL). N,N-diisopropylethylamine (173 µL, 0.99 mmol) and 1-methyl-1H-pyrazol-3-ylamine (32 µL, 0.33 mmol) were added and the reaction mixture was cooled to 0° C. O-(7-Azabenzotriazole-1-yl)-N,N,N'N'-tetramethyluronium hexafluorophosphate (126 mg, 0.33 mmol) was added and the reaction mixture was allowed to warm to 25° C. After stirring 16 h, the reaction mixture was diluted with chloroform (2 mL) and washed with saturated aqueous sodium bicarbonate solution (1.5 mL). The aqueous phase was extracted with chloroform (1.5 mL) and the combined organic phases were filtered through sodium sulfate and evaporated in vacuo. The residue was purified by flash column chromatography (Merck silica gel 60, 40-63 µm; 40% ethyl acetate/hexanes) to afford (E)-2-cyclopentyloxyimino-2-(3,4-dichloro-phenyl)-N-(1-methyl-1H-pyrazol-3-yl)-acetamide (103 mg, 82%) as a white solid after lyophilization from aqueous dioxane: LC-MS (ESI) m/e calcd for $C_{17}H_{18}Cl_2N_4O_2$ [M$^+$] 380.08, found 381 [M+H$^+$]; H$^1$-NMR (400 MHz, CDCl$_3$) □ ppm 1.64 (m, 4 H, 2×CH$_2$), 1.85 (m, 4 H, 2×CH$_2$), 3.83 (s, 3 H, NCH$_3$), 4.84 (m, 1 H, OCH), 6.70 (d, J=2.3 Hz, 1 H, Ar), 7.26 (d, J=2.3 Hz, 1 H, Ar), 7.33 (dd, Jo=8.3, Jm=1.9 Hz, 1 H, Ar), 7.47 (d, Jo=8.3 Hz, 1 H, Ar), 7.61 (d, Jm=1.9 Hz, 1 H, Ar), 9.15 (s, 1 H, NH).

Example 19

(E)-N-Benzothiazol-2-yl-2-cyclopentyloxyimino-2-(3,4-dichloro-phenyl)-acetamide

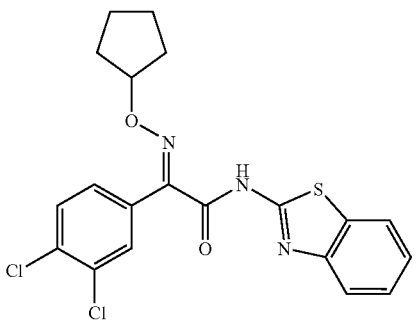

(E)-Cyclopentyloxyimino-(3,4-dichloro-phenyl)-acetic acid (prepared as in Example 18, 100 mg, 0.33 mmol), 2-aminobenzothiazole (50 mg 0.33 mmol) and N,N-diisopropylethylamine (173 μL, 0.99 mmol) were combined in methylene chloride (1.6 mL) and cooled in an ice bath. O-(7-Azabenzotriazole-1-yl)-N,N,N'N'-tetramethyluronium hexafluorophosphate (126 mg, 0.33 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 40% ethyl acetate/hexanes) to afford (E)-N-benzothiazol-2-yl-2-cyclopentyloxyimino-2-(3,4-dichloro-phenyl)-acetamide (96 mg, 67%) as a white solid after lyophilization from aqueous acetonitrile: LC-MS (ESI) m/e calcd for $C_{20}H_{17}Cl_2N_3O_2S$ [M+] 433.04, found 434 [M+H+]; $H^1$-NMR (400 MHz, CDCl$_3$) δ ppm 1.68 (m, 4 H, 2×CH$_2$), 1.90 (m, 4 H, 2×CH$_2$), 4.93 (m, 1 H, OCH), 7.34 (ddd, Jo=8.0, Jo=7.3, Jm=1.2 Hz, 1 H, Ar), 7.40 (dd, Jo=8.4, Jm=2.0 Hz, 1 H, Ar), 7.47 (ddd, Jo=8.3, Jo=7.3, Jm=1.3 Hz, 1 H, Ar), 7.53 (d, Jo=8.4 Hz, 1 H, Ar), 7.67 (d, Jm=2.0 Hz, 1 H, Ar), 7.83 (m, 2H, Ar), 10.20 (s, 1 H, NH).

Example 20

(E)-N-Benzothiazol-2-yl-2-cyclopentyloxyimino-2-(4-methanesulfonyl-phenyl)-acetamide

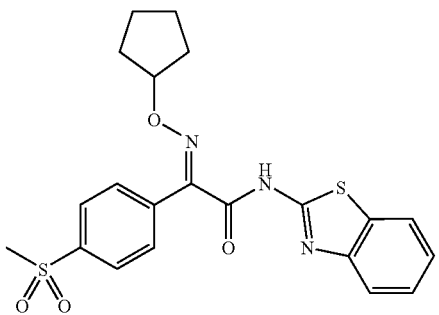

(4-Methylsulfanyl-phenyl)-oxo-acetic acid ethyl ester (1.09 g, 4.86 mmol) and oxone (8.96 g, 14.6 mmol) were combined in a mixture of water (2.2 mL) and methanol (22 mL) and stirred for 16 h. The volatiles were evaporated in vacuo and the residue was treated with water (50 mL) and extracted with ethyl acetate (3×50 mL). The combined organic phases were dried over magnesium sulfate and evaporated in vacuo. The residue was purified by flash column chromatography (Merck silica gel 60, 40-63 μm; 33% ethyl acetate/hexanes) to afford (4-methanesulfonyl-phenyl)-oxo-acetic acid ethyl ester as a white solid (261 mg, 21%): $H^1$-NMR (400 MHz, CDCl$_3$) δ=1.46 (3H, t, J=7.1 Hz), 3.10 (3H, s), 4.48 (2H, q, J=7.1 Hz), 8.09 (2H, m), 8.23 (2H, m).

(4-Methylsulfonyl-phenyl)-oxo-acetic acid ethyl ester (218 mg, 0.85 mmol) was stirred in ethanol (1.7 mL) and warmed in a 70° C. oil bath. O-Cyclopentyl-hydroxylamine (prepared as in Example 1, 146 mg, 1.06 mmol) was added. After 2 h, the reaction mixture was allowed to cool and concentrated in vacuo. Purification by flash column chromatography (Merck silica gel 60, 40-63 □m; 30% ethyl acetate/hexanes to 75% ethyl acetate/hexanes) afforded (E)-cyclopentyloxyimino-(4-methanesulfonyl-phenyl)-acetic acid ethyl ester (60 mg, 21%) as a clear, colorless film containing an unidentified impurity: LC-MS (ESI) m/e calcd for $C_{16}H_{21}NO_5S$ [M+] 339.11, found 340 [M+H+].

(E)-Cyclopentyloxyimino-(4-methanesulfonyl-phenyl)-acetic acid ethyl ester (60 mg, 0.18 mmol) was dissolved in ethanol (1.75 mL) and cooled to 0° C. A 2.0 N solution of lithium hydroxide in water (258 μL, 0.52 mmol) was added dropwise and the cooling bath was removed. After stirring 40 min, the reaction mixture was diluted with chloroform (30 mL) and washed with 0.2 M aqueous potassium bisulfate (20 mL). The aqueous phase was extracted with chloroform (30 mL) and the combined organic phases were dried over magnesium sulfate and evaporated in vacuo to afford (E)-cyclopentyloxyimino-(4-methanesulfonyl-phenyl)-acetic acid as a clear, colorless film that was used without further purification.

(E)-Cyclopentyloxyimino-(4-methanesulfonyl-phenyl)-acetic acid (37 mg, 0.12 mmol), N,N-diisopropylethylamine (92 μL, 0.53 mmol) and 2-aminobenzothiazole (27 mg, 0.18 mmol) were combined in methylene chloride (2 mL) and cooled to 0° C. O-(7-Azabenzotriazole-1-yl)-N,N,N'N'-tetramethyluronium hexafluorophosphate (67 mg, 0.18 mmol) was added and the cooling bath was removed. After stirring 16 h, the reaction mixture was diluted with chloroform (2 mL) and washed with saturated aqueous sodium bicarbonate solution (1.5 mL). The aqueous phase was extracted with chloroform (1.5 mL) and the combined organic phases were filtered through sodium sulfate and evaporated in vacuo. The residue was purified by flash column chromatography (Merck silica gel 60, 40-63 μm; 40% ethyl acetate/hexanes) to afford (E)-N-benzothiazol-2-yl-2-cyclopentyloxyimino-2-(4-methanesulfonyl-phenyl)-acetamide (34 mg, 43%) as a white solid: LC-MS (ESI) m/e calcd for $C_{21}H_{21}N_3O_4S_2$ [M+] 443.10, found 444 [M+H+]; $H^1$-NMR (400 MHz, CDCl$_3$) δ ppm 1.66 (m, 4 H, 2×CH$_2$), 1.90 (m, 4 H, 2×CH$_2$), 3.11 (s, 3 H, SO$_2$CH$_3$), 4.95 (m, 1 H, OCH), 7.35 (brt, 1 H, Ar), 7.48 (brt, 1 H, Ar), 7.72 (d, J=8.4 Hz, 2 H, Ar), 7.83 (m, 2H, Ar), 8.03 (d, J=8.4 Hz, 2 H, Ar), 10.24 (s, 1 H, NH).

Example 21

(E)-2-(3-Chloro-4-methanesulfonyl-phenyl)-2-cyclopentyloxyimino-N-(5-methyl-thiazol-2-yl)-acetamide

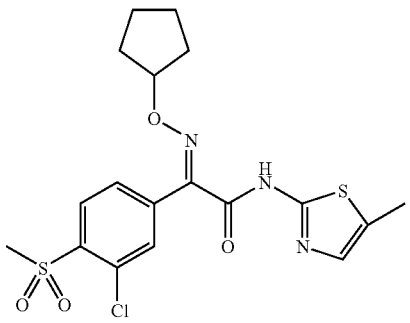

(E)-(3-Chloro-4-methanesulfonyl-phenyl)-cyclopentyloxyimino-acetic acid (prepared as in Example 1, 84 mg, 0.24 mmol), 5-methyl-thiazol-2-ylamine (28 mg, 0.24 mmol) and N,N-diisopropylethylamine (127 μL, 0.73 mmol) were combined in methylene chloride (2 mL) and cooled in an ice bath. O-(7-Azabenzotriazole-1-yl)-N,N,N'N'-tetramethyluronium hexafluorophosphate (92 mg, 0.24 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 40% ethyl acetate/hexanes) to afford (E)-2-(3-chloro-4-methanesulfonyl-phenyl)-2-cyclopentyloxyimino-N-(5-methyl-thiazol-2-yl)-acetamide (74 mg, 69%) as a white solid after lyophilization from aqueous acetonitrile: LC-MS (ESI) m/e calcd for $C_{18}H_{20}ClN_3O_4S_2$ $[M^+]$ 441.06, found 442 $[M+H^+]$; $H^1$-NMR (400 MHz, CDCl$_3$) δ ppm 1.66 (m, 4 H, 2×CH$_2$), 1.89 (m, 4 H, 2×CH$_2$), 2.45 (d, J=1.2 Hz, 3 H, ArCH$_3$), 3.31 (s, 3 H, SO$_2$CH$_3$), 4.93 (m, 1 H, OCH), 7.15 (brq, 1 H, Ar), 7.59 (dd, Jo=8.2, Jm=1.5 Hz, 1 H, Ar), 7.70 (d, Jm=1.5 Hz, 1 H, Ar), 8.21 (d, Jo=8.2 Hz, 1 H, Ar), 10.03 (s, 1 H, NH).

Example 22

(E)-2-(3-Chloro-4-methanesulfonyl-phenyl)-2-cyclopentyloxyimino-N-(6-methoxy-benzothiazol-2-yl)-acetamide

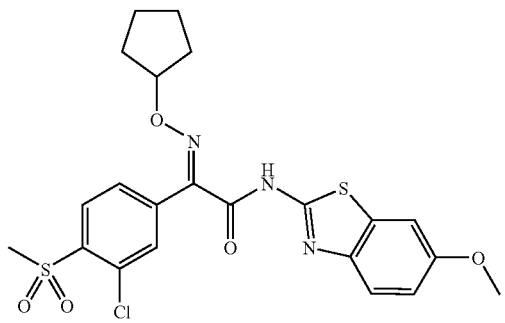

(E)-(3-Chloro-4-methanesulfonyl-phenyl)-cyclopentyloxyimino-acetic acid (prepared as in Example 1, 84 mg, 0.24 mmol), 6-methoxy-2-aminobenzothiazole (44 mg, 0.24 mmol) and N,N-diisopropylethylamine (127 μL, 0.73 mmol) were combined in methylene chloride (2 mL) and cooled in an ice bath. O-(7-Azabenzotriazole-1-yl)-N,N,N'N'-tetramethyluronium hexafluorophosphate (92 mg, 0.24 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 40% ethyl acetate/hexanes) to afford (E)-2-(3-chloro-4-methanesulfonyl-phenyl)-2-cyclopentyloxyimino-N-(6-methoxy-benzothiazol-2-yl)-acetamide (67 mg, 54%) as a faintly yellow solid after lyophilization from aqueous acetonitrile: LC-MS (ESI) m/e calcd for $C_{22}H_{22}ClN_3O_5S_2$ $[M^+]$ 507.07, found 508 $[M+H^+]$; $H^1$-NMR (400 MHz, CDCl$_3$) δ ppm 1.67 (m, 4 H, 2×CH$_2$), 1.90 (m, 4 H, 2×CH$_2$), 3.32 (s, 3 H, SO$_2$CH$_3$), 3.89 (d, 3 H, OCH$_3$), 4.96 (m, 1 H, OCH), 7.07 (dd, Jo=8.9, Jm=2.5 Hz, 1 H, Ar), 7.31 (d, Jm=2.5 Hz, 1 H, Ar), 7.61 (dd, Jo=8.2, Jm=1.5 Hz, 1 H, Ar), 7.70 (d, Jo=8.9 Hz, 1 H, Ar), 7.71 (d, Jm=1.5 Hz, 1 H, Ar), 8.22 (d, Jo=8.2 Hz, 1 H, Ar), 10.11 (s, 1 H, NH).

Example 23

(E)-N-(6-Chloro-benzothiazol-2-yl)-2-(3-chloro-4-methanesulfonyl-phenyl)-2-cyclopentyloxyimino-acetamide

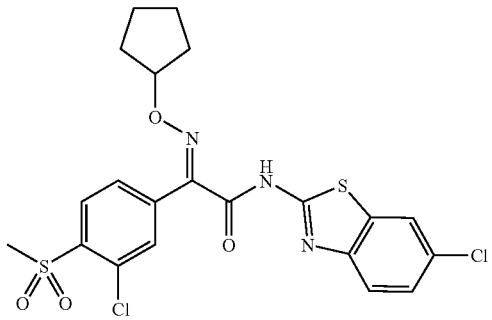

(E)-(3-chloro-4-methanesulfonyl-phenyl)-cyclopentyloxyimino-acetic acid (prepared as in Example 1, 84 mg, 0.24 mmol), 6-chloro-2-aminobenzothiazole (45 mg, 0.24 mmol) and N,N-diisopropylethylamine (127 μL, 0.73 mmol) were combined in methylene chloride (2 mL) and cooled in an ice bath. O-(7-Azabenzotriazole-1-yl)-N,N,N'N'-tetramethyluronium hexafluorophosphate (92 mg, 0.24 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 33% ethyl acetate/hexanes) to afford (E)-N-(6-chloro-benzothiazol-2-yl)-2-(3-chloro-4-methanesulfonyl-phenyl)-2-cyclopentyloxyimino-acetamide (66 mg, 53%) as a white solid after lyophilization from aqueous acetonitrile: LC-MS (ESI) m/e calcd for $C_{21}H_{19}Cl_2N_3O_4S_2$ $[M^+]$ 511.02, found 512 $[M+H^+]$; $H^1$-NMR (400 MHz, CDCl$_3$) δ ppm 1.68 (m, 4 H, 2×CH$_2$), 1.91 (m, 4 H, 2×CH$_2$), 3.32 (s, 3 H, SO$_2$CH$_3$), 4.97 (m, 1 H, OCH), 7.43 (dd, Jo=8.6, Jm=2.1 Hz, 1 H, Ar), 7.60 (dd, Jo=8.2, Jm=1.5 Hz, 1 H, Ar), 7.71 (m, 2 H, Ar), 7.81 (m, 1 H, Ar), 8.23 (d, Jo=8.2 Hz, 1 H, Ar), 10.18 (s, 1 H, NH).

Example 24

(E)-2-(3-Chloro-4-methanesulfonyl-phenyl)-2-isobutoxyimino-N-(1-methyl-1H-pyrazol-3-yl)-acetamide

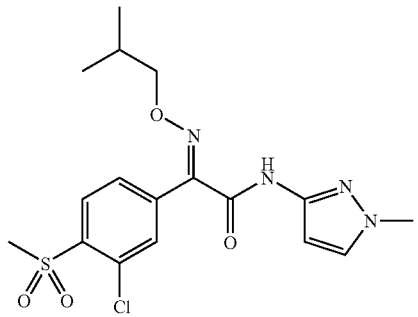

(3-Chloro-4-methanesulfonyl-phenyl)-oxo-acetic acid methyl ester (prepared as in Example 1, 90 mg, 3.26 mmol) was stirred in methanol (7 mL) and warmed in a 70° C. oil bath. O-Isobutylhydroxylamine hydrochloride (511 mg, 4.07 mmol) was added. After 3 h, the reaction mixture was allowed to cool and concentrated in vacuo. Purification by flash column chromatography (Merck silica gel 60, 40-63 μm; 20% ethyl acetate/hexanes to 30% ethyl acetate/hexanes) afforded (E)-(3-chloro-4-methanesulfonyl-phenyl)-isobutoxyimino-acetic acid methyl ester as a white solid (395 mg, 35%): $H^1$-NMR (400 MHz, $CDCl_3$) δ=0.91 (6H, d, J=6.8 Hz), 2.04 (1H, m), 3.30 (3H, s), 3.91 (3H, s), 4.10 (2H, d, J=6.8 Hz), 7.50 (1H, dd, J=8.2 Hz, J=1.6 Hz), 7.61 (1H, d, J=1.6 Hz), 8.18 (1H, d, J=8.2 Hz).

(E)-(3-Chloro-4-methanesulfonyl-phenyl)-isobutoxy-imino-acetic acid methyl ester (326 mg, 0.94 mmol) was dissolved in methanol (9.4 mL) and cooled to 0° C. A 2.0 N aqueous solution of lithium hydroxide (1.41 mL, 2.82 mmol) was added dropwise and the cooling bath was removed. After stirring 25 min, the reaction mixture was diluted with chloroform (175 mL) and washed with 0.2 M aqueous potassium bisulfate solution (50 mL). The aqueous phase was extracted with chloroform (75 mL) and the combined organic phases were dried over magnesium sulfate and evaporated in vacuo to afford (E)-(3-chloro-4-methanesulfonyl-phenyl)-isobutoxyimino-acetic acid as a faintly yellow semi-solid (352 mg, >100%), which was used without further purification.

(E)-(3-Chloro-4-methanesulfonyl-phenyl)-isobutoxy-imino-acetic acid (104 mg, 0.31 mmol), 1-methyl-1H-pyrazol-3-ylamine (30 mg, 0.31 mmol) and N,N-diisopropylethylamine (163 µL, 0.94 mmol) were combined in methylene chloride (1.5 mL) and cooled in an ice bath. O-(7-Azabenzotriazole-1-yl)-N,N,N'N'-tetramethyluronium hexafluorophosphate (119 mg, 0.31 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 50% ethyl acetate/hexanes) to afford (E)-2-(3-chloro-4-methanesulfonyl-phenyl)-2-isobutoxy-imino-N-(1-methyl-1H-pyrazol-3-yl)-acetamide (122 mg, 95%) as a white solid after lyophilization from aqueous acetonitrile: LC-MS (ESI) m/e calcd for $C_{17}H_{21}ClN_4O_4S$ [$M^+$] 412.10, found 413 [$M+H^+$]; $H^1$-NMR (400 MHz, $CDCl_3$) δ ppm 0.94 (d, J=6.7 Hz, 6 H, 2×$CH_3$), 2.05 (m, 1 H, CH), 3.29 (s, 3 H, $SO_2CH_3$), 3.84 (s, 3 H, $NCH_3$), 4.06 (d, J=6.8 Hz, 2 H, $OCH_2$), 6.68 (d, J=2.3 Hz, 1 H, Ar), 7.28 (d, J=2.3 Hz, 1 H, Ar), 7.58 (dd, Jo=8.2, Jm=1.5 Hz, 1 H, Ar), 7.69 (d, Jm=1.5 Hz, 1 H, Ar), 8.19 (d, Jo=8.2 Hz, 1 H, Ar), 9.13 (brs, 1 H, NH).

Example 25

(E)-N-Benzothiazol-2-yl-2-(3-chloro-4-methanesulfonyl-phenyl)-2-isobutoxyimino-acetamide

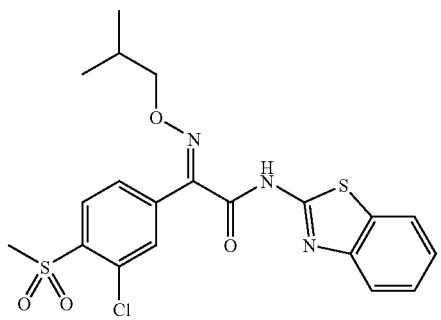

(E)-(3-chloro-4-methanesulfonyl-phenyl)-isobutoxy-imino-acetic acid (prepared as in Example 24, 104 mg, 0.31 mmol), 2-aminobenzothiazole (47 mg, 0.31 mmol) and N,N-diisopropylethylamine (163 µL, 0.94 mmol) were combined in methylene chloride (1.5 mL) and cooled in an ice bath. O-(7-Azabenzotriazole-1-yl)-N,N,N'N'-tetramethyluronium hexafluoro-phosphate (119 mg, 0.31 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 30% ethyl acetate/hexanes) to afford (E)-N-benzothiazol-2-yl-2-(3-chloro-4-methanesulfonyl-phenyl)-2-isobutoxyimino-acetamide (86 mg, 60%) as a white solid after lyophilization from aqueous acetonitrile: LC-MS (ESI) m/e calcd for $C_{20}H_{20}ClN_3O_4S_2$ [$M^+$] 465.06, found 466 [$M+H^+$]; $H^1$-NMR (400 MHz, $CDCl_3$) δ ppm 0.97 (d, J=6.6 Hz, 6 H, 2×$CH_3$), 2.09 (m, 1 H, CH), 3.32 (s, 3 H, $SO_2CH_3$), 4.12 (d, J=6.8 Hz, 2 H, $OCH_2$), 7.35 (brt, J=7.8 Hz, 1H, Ar), 7.48 (brt, J=7.8 Hz, 1H, Ar), 7.63 (dd, Jo=8.2, Jm=1.6 Hz, 1 H, Ar), 7.74 (d, Jm=1.6 Hz, 1 H, Ar), 7.83 (m, 2H, Ar), 8.24 (d, Jo=8.2 Hz, 1 H, Ar), 10.25 (brs, 1 H, NH).

Example 26

(E)-2-(3-Chloro-4-methanesulfonyl-phenyl)-2-cyclopentyloxyimino-N-(5-methyl-[1,3,4]thiadiazol-2-yl)-acetamide

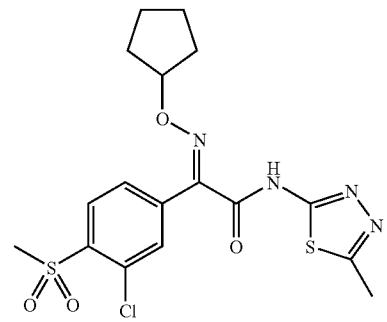

(E)-(3-Chloro-4-methanesulfonyl-phenyl)-cyclopentyloxyimino-acetic acid (prepared as in Example 1, 100 mg, 0.29 mmol), 5-methyl-[1,3,4]thiadiazol-2-ylamine (37 mg, 0.32 mmol) and N,N-diisopropylethylamine (166 µL, 0.95 mmol) were combined in methylene chloride (2 mL) and cooled in an ice bath. O-(7-Azabenzotriazole-1-yl)-N,N,N'N'-tetramethyluronium hexafluorophosphate (121 mg, 0.32 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 60% ethyl acetate/hexanes) to afford (E)-2-(3-chloro-4-methanesulfonyl-phenyl)-2-cyclopentyloxyimino-N-(5-methyl-[1,3,4]thiadiazol-2-yl)-acetamide (58 mg, 45%) as a white solid after lyophilization from aqueous acetonitrile: LC-MS (ESI) m/e calcd for $C_{17}H_{19}ClN_4O_4S$ [$M^+$] 442.05, found 443

[M+H⁺]; H¹-NMR (400 MHz, CDCl₃) δ ppm 1.67 (m, 4 H, 2×CH₂), 1.89 (m, 4 H, 2×CH₂), 2.75 (s, 3 H, ArCH₃), 3.32 (s, 3 H, SO₂CH₃), 4.97 (m, 1 H, OCH), 7.58 (dd, Jo=8.2, Jm=1.5 Hz, 1 H, Ar), 7.68 (d, Jm=1.5 Hz, 1 H, Ar), 8.22 (d, Jo=8.2 Hz, 1 H, Ar), 10.33 (brs, 1 H, NH).

Example 27

(E)-N-(3-Benzyl-[1,2,4]thiadiazol-5-yl)-2-(3-chloro-4-methanesulfonyl-phenyl)-2-cyclopentyloxyimino-acetamide

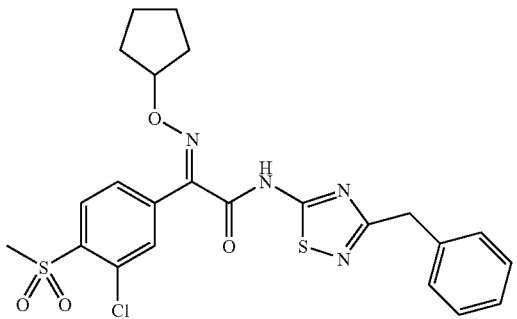

Ammonium chloride (1.60 g, 29.9 mmol) was slurried in toluene (30 mL) and cooled to 0° C. A 2.0 M solution of trimethylaluminum in toluene (15 mL, 30 mmol) was added dropwise and the cooling bath was removed. After stirring 1.5 h, a solution of benzyl cyanide (1.15 mL, 9.96 mmol) in toluene (20 mL) was added dropwise. The reaction mixture was heated to 80° C. for 16 h, then allowed to cool and poured carefully into a slurry of Merck silica gel 60, 40-63 μm (22 g) in chloroform (75 mL). After stirring 5 min, this slurry was filtered and the cake was washed with methanol (2×75 mL). The combined filtrates were concentrated in vacuo to precipitate ammonium chloride, which was removed by filtration. To the resulting filtrate, was added a 4.0 M solution of hydrochloric acid in dioxane (7 mL, 28 mmol). The resulting mixture was added to diethyl ether (220 mL) and isopropyl alcohol and this mixture was then concentrated in vacuo. The residue was stirred in diethyl ether (100 mL) for 10 min and then allowed to stand. The supernatant was poured off and the residue was dried in vacuo to afford 2-phenyl-acetamidine hydrochloride (1.6 g) as a faintly yellow paste contaminated with ammonium chloride and isopropyl alcohol. This was used without further purification.

The crude 2-phenyl-acetamidine hydrochloride (1.32 g, 7.74 mmol) was dissolved in water (10 mL) and cooled to 0° C. A ~1.7 M solution of sodium hypochlorite in water (3.68 mL, 6.26 mmol) was added dropwise. The reaction mixture was stirred 1 h, then solid sodium chloride was added to saturate the aqueous phase, which was extracted with ethyl acetate (2×25 mL). The combined organic phases were filtered through sodium sulfate and evaporated in vacuo. The residue was purified by flash column chromatography (Merck silica gel 60, 40-63 μm; 33% ethyl acetate/hexanes) to afford N-chloro-2-phenyl-acetamidine (155 mg, 9% over two steps) as an off-white semi-solid: H¹-NMR (400 MHz, CDCl₃) δ=3.67 (2H, s), 5.13 (2H, br), 7.31 (5H, m).

N-Chloro-2-phenyl-acetamidine (154 mg, 0.92 mmol) was dissolved in methanol (4.6 mL) and cooled to 0° C. then potassium thiocyanate (89 mg, 0.92 mmol) was added and it was stirred for 1 h. The mixture was diluted with ethyl acetate (50 mL), stirred for 5 min and filtered. The filtrate was evaporated in vacuo and the residue was purified by flash column chromatography (Merck silica gel 60, 40-63 μm; 50% ethyl acetate/hexanes) to afford 3-benzyl-[1,2,4]thiadiazol-5-ylamine (93 mg, 53%) as an off-white solid: H¹-NMR (400 MHz, CDCl₃) δ=4.02 (2H, s), 5.94 (2H, br), 7.28 (5H, m).

(E)-(3-Chloro-4-methanesulfonyl-phenyl)-cyclopentyl-oxyimino-acetic acid (prepared as in Example 1, 100 mg, 0.29 mmol), 3-benzyl-[1,2,4]thiadiazol-5-ylamine (55 mg, 0.29 mmol) and N,N-diisopropylethylamine (166 μL, 0.95 mmol) were combined in methylene chloride (1.5 mL) and cooled in an ice bath. O-(7-Azabenzotriazole-1-yl)-N,N,N'N'-tetramethyluronium hexafluorophosphate (121 mg, 0.32 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 33% ethyl acetate/hexanes) to afford (E)-N-(3-benzyl-[1,2,4]thiadiazol-5-yl)-2-(3-chloro-4-methanesulfonyl-phenyl)-2-cyclopentyl-oxyimino-acetamide (26 mg, 17%) as a white solid after lyophilization from aqueous acetonitrile: LC-MS (ESI) m/e calcd for C₂₃H₂₃ClN₄O₄S₂ [M⁺] 518.08, found 519 [M+H⁺]; H¹-NMR (400 MHz, CDCl₃) δ ppm 1.67 (m, 4 H, 2×CH₂), 1.89 (m, 4 H, 2×CH₂), 3.31 (s, 3 H, SO₂CH₃), 4.24 (s, 2 H, CH₃), 4.93 (m, 1 H, OCH), 7.23-7.28 (m, 1 H, Ar), 7.29-7.36 (m, 4 H, Ar), 7.58 (dd, Jo=8.2, Jm=1.6 Hz, 1 H, Ar), 7.68 (d, Jm=1.6 Hz, 1 H, Ar), 8.22 (d, Jo=8.2 Hz, 1 H, Ar), 10.33 (s, 1 H, NH).

Example 28

(E)-2-(3-Chloro-4-methanesulfonyl-phenyl)-2-cyclopentyloxyimino-N-(1-propyl-1H-pyrazol-3-yl)-acetamide

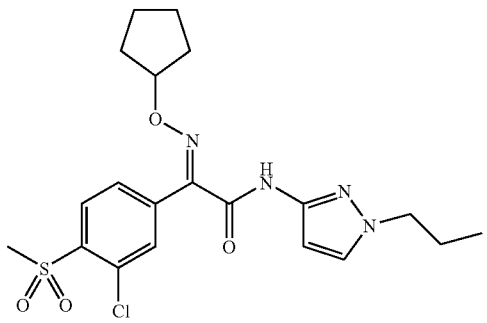

3-Nitro-1H-pyrazole (prepared as in Example 15, 100 mg, 0.89 mmol) was dissolved in anhydrous N,N-dimethylformamide (4 mL) and a 60% dispersion of sodium hydride in mineral oil (37 mg, 0.93 mmol) was added while stirring under nitrogen. After the effervescence ceased and the mixture stirred for an additional 10 min, the 1-bromo-propane (91 μL, 1.00 mmol) was added. The mixture continued to stir under nitrogen for 16 h. The solution was diluted with ethyl acetate (50 mL), washed with water (2×20 mL), saturated aqueous brine solution (2×20 mL), dried over magnesium sulfate, filtered and concentrated in vacuo. Purification by ISCO flash column chromatography (Teledyne Isco RediSep Flash Column 10 g; 25% ethyl acetate/hexanes to 75% ethyl acetate/hexanes) afforded 3-nitro-1-propyl-1H-pyrazole (92 mg, 67%) as a yellow oil: $H^1$-NMR (400 MHz, $CDCl_3$) δ 0.89 (3H, t, J=7.6 Hz), 1.90 (2H, sextet, J=7.2 Hz), 6.82 (1H, d, J=2.8 Hz), 7.44 (1H, d, J=2.4 Hz).

3-Nitro-1-propyl-1H-pyrazole (92 mg, 0.59 mmol) was dissolved in ethyl acetate (3 mL) and methanol (3 mL) was added. Palladium, 10 wt. % on carbon, wet (~50 mg) was added to the mixture. The vial was charged with hydrogen gas (via balloon) and the mixture stirred for 16 h at 25° C. The mixture was passed through a plug of celite and concentrated in vacuo followed by purification by flash column chromatography (Merck silica gel 60, 40-63 µm; 25% ethyl acetate/hexanes to 70% ethyl acetate/hexanes) afforded 1-propyl-1H-pyrazol-3-ylamine (54 mg, 73%) as a golden oil: LC-MS (ESI) m/e calcd for $C_6H_{11}N_3$ [M+] 125.10, found 126.3 [M+H+], 251.3 [2M+H+].

(E)-(3-Chloro-4-methanesulfonyl-phenyl)-cyclopentyloxyimino-acetic acid (prepared as in Example 1, 100 mg, 0.29 mmol), 1-propyl-1H-pyrazol-3-ylamine (40 µL, 0.29 mmol) and N,N-diisopropylethylamine (151 µL, 0.87 mmol) were combined in methylene chloride (1.5 mL) and cooled in an ice bath. O-(7-Azabenzotriazole-1-yl)-N,N,N'N'-tetramethyluronium hexafluorophosphate (110 mg, 0.29 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 33% ethyl acetate/hexanes) to afford (E)-2-(3-chloro-4-methanesulfonyl-phenyl)-2-cyclopentyloxyimino-N-(1-propyl-1H-pyrazol-3-yl)-acetamide (88 mg, 67%) as a white solid after lyophilization from aqueous acetonitrile: LC-MS (ESI) m/e calcd for $C_{20}H_{25}ClN_4O_4S$ [M+] 452.13, found 453 [M+H+]; $H^1$-NMR (400 MHz, $CDCl_3$) δ ppm 0.98 (t, J=7.5 Hz, 3H, $CH_3$), 1.64 (m, 4 H, 2×$CH_2$), 1.87 (m, 6 H, 3×$CH_2$), 3.29 (s, 3 H, $SO_2CH_3$), 4.01 (st, J=7.0 Hz, 32H, $NCH_2$), 4.88 (m, 1 H, OCH), 6.69 (d, J=2.3 Hz, 1 H, Ar), 7.31 (d, J=2.3 Hz, 1 H, Ar), 7.55 (dd, Jo=8.2, Jm=1.6 Hz, 1 H, Ar), 7.66 (d, Jm=1.6 Hz, 1 H, Ar), 8.18 (d, Jo=8.2 Hz, 1 H, Ar), 9.16 (s, 1 H, NH).

Example 29

(E)-N-(5-Benzyl-[1,3,4]thiadiazol-2-yl)-2-(3-chloro-4-methanesulfonyl-phenyl)-2-cyclopentyloxyimino-acetamide

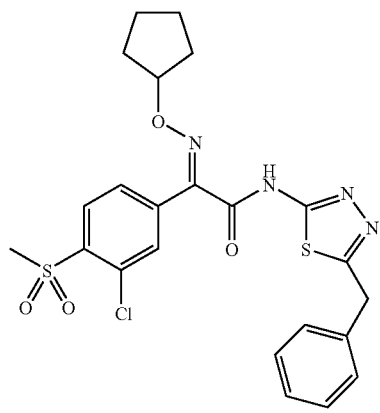

(m, 5 H, (E)-(3-Chloro-4-methanesulfonyl-phenyl)-cyclopentyl-oxyimino-acetic acid (prepared as in Example 1, 100 mg, 0.29 mmol), 5-benzyl-[1,3,4]thiadiazol-2-ylamine (55 mg, 0.29 mmol) and N,N-diisopropylethylamine (151 µL, 0.87 mmol) were combined in methylene chloride (1.5 mL) and cooled in an ice bath. O-(7-Azabenzotriazole-1-yl)-N,N,N'N'-tetramethyluronium hexafluorophosphate (110 mg, 0.29 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 µm; 50% ethyl acetate/hexanes) to afford (E)-N-(5-benzyl-[1,3,4]thiadiazol-2-yl)-2-(3-chloro-4-methanesulfonyl-phenyl)-2-cyclopentyl-oxyimino-acetamide (97 mg, 64%) as a white solid after lyophilization from aqueous acetonitrile: LC-MS (ESI) m/e calcd for $C_{23}H_{23}ClN_4O_4S_2$[M+] 518.08, found 519 [M+H+]; $H^1$-NMR (400 MHz, $CDCl_3$) δ ppm 1.66 (m, 4 H, 2×$CH_2$), 1.89 (m, 4 H, 2×$CH_2$), 3.30 (s, 3 H, $SO_2CH_3$), 4.38 (s, 2 H, $CH_3$), 4.97 (m, 1 H, OCH), 7.24-7.36Ar), 7.55 (dd, Jo=8.2, Jm=1.6 Hz, 1 H, Ar), 7.65 (d, Jm=1.6 Hz, 1 H, Ar), 8.19 (d, Jo=8.2 Hz, 1 H, Ar), 10.29 (s, 1 H, NH).

Example 30

(E)-N-[1-(3-Acetylamino-benzyl)-1H-pyrazol-3-yl]-2-(3-chloro-4-methanesulfonyl-phenyl)-2-cyclopentyloxyimino-acetamide

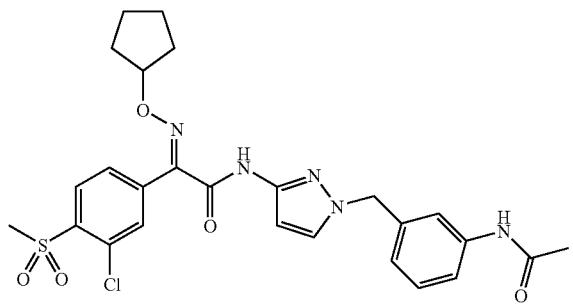

(3-Amino-phenyl)-methanol (3 g, 24.6 mmol) was dissolved in tetrahydrofuran (125 mL). Sodium bicarbonate (6.3 g, 75 mmol) was added followed by acetyl chloride (1.77 mL, 25 mmol). The mixture stirred at 25° C. for 16 h. The mixture was poured into ice water and the product precipitated as a white solid. Collection by vacuum filtration followed by drying in vacuo afforded the desired product, N-(3-hydroxymethyl-phenyl)-acetamide (3.44 g, 85% yield) as a white powder: $H^1$-NMR (400 MHz, DMSO-$d_6$) δ 2.02 (3H, s), 4.44 (2H, d, J=6.2 Hz), 5.14 (1H, t, J=5.9 Hz), 6.94 (1H, d, J=7.2 Hz), 7.19 (1H, t, J=7.8 Hz), 7.43 (1H, d, J=8.0 Hz), 7.51 (1H, s), 9.84 (1H, s).

N-(3-Hydroxymethyl-phenyl)-acetamide (2.75 g, 16.77 mmol) and triphenylphosphine (6.62 g, 25.24 mmol) were combined and dissolved in methylene chloride (66 mL). Tetrabromomethane (8.37 g, 25.24 mmol) was dissolved in acetonitrile (22 mL) and added dropwise to the stirring solution. The mixture stirred at 25° C. for 5 h. The mixture was concentrated in vacuo to a golden oil. Purification by flash column chromatography (Merck silica gel 60, 40-63 µm; 40% ethyl acetate/hexanes) afforded the desired product, N-(3- bromomethyl-phenyl)-acetamide (2.8 g, 74% yield) as an oil: H$^1$-NMR (400 MHz, DMSO-d$_6$) δ 2.03 (3H, s), 4.65 (2H, s), 7.08 (1H, d, J=7.8 Hz), 7.24 (1H, t, J=7.8 Hz), 7.45 (1H, d, J=9.6 Hz), 7.68 (1H, s), 9.96 (1H, s).

3-Nitro-1H-pyrazole (prepared as in Example 15, 1.24 g, 11.0 mmol) was dissolved in anhydrous N,N-dimethylformamide (25 mL) and a 60% suspension of sodium hydride in mineral oil (426 mg, 11.55 mmol) was added. The mixture bubbled and stirred at 25° C. for 20 min. N-(3-Bromomethyl-phenyl)-acetamide (1.5 g, 5.26 mmol) was added and the mixture continued to stir at 25° C. for 20 min. The mixture was diluted with ethyl acetate, washed with water, a saturated brine solution, dried over magnesium sulfate and concentrated in vacuo to a yellow oil. Purification by flash column chromatography (Merck silica gel 60, 40-63 μm; 5% ethyl acetate/hexanes to 50% ethyl acetate/hexanes) afforded the desired product, N-[3-(3-nitro-pyrazol-1-ylmethyl)-phenyl]-acetamide (1.81 g, 63% yield) as an off white solid: H$^1$-NMR (400 MHz, DMSO-d$_6$) δ 2.01 (3H, s), 5.42 (2H, s), 6.96 (1H, d, J=7.9 Hz), 7.06 (1H, d, J=2.4 Hz), 7.27 (1H, t, J=7.8 Hz), 7.45 (1H, s), 7.52 (1H, d, J=7.9 Hz), 8.12 (1H, d, J=2.4 Hz), 9.93 (1H, s).

N-[3-(3-Nitro-pyrazol-1-ylmethyl)-phenyl]-acetamide (1.75 g, 6.73 mmol) was dissolved in ethyl acetate (15 mL) and methanol (15 mL) was added. While stirring, a 50% slurry of Raney Nickel (4 mL) was added followed by hydrazine (1.5 mL). Immediate effervescence was observed. The mixture continued to stir and bubble for 30 min. The mixture was passed through a plug of celite followed by a plug of silica gel, eluting with ethyl acetate. The filtrate was concentrated in vacuo to afford the desired product, N-[3-(3-amino-pyrazol-1-ylmethyl)-phenyl]-acetamide (1.46 g, 94%) as a beige powder: H$^1$-NMR (400 MHz, DMSO-d6) δ 2.01 (3H, s), 4.51 (2H, bs), 4.96 (2H, s), 5.39 (1H, d, J=2.6 Hz), 6.82 (1H, d, J=8.1 Hz), 7.19 (1H, t, J=7.8 Hz), 7.35 (1H, s), 7.38 (1H, d, J=2.3 Hz), 7.47 (1H, d, J=7.5 Hz), 9.90 (1H, s).

(E)-(3-Chloro-4-methanesulfonyl-phenyl)-cyclopentyloxyimino-acetic acid (prepared as in Example 1, 100 mg, 0.29 mmol), N-[3-(3-amino-pyrazol-1-ylmethyl)-phenyl]-acetamide (67 mg, 0.29 mmol) and N,N-diisopropylethylamine (151 μL, 0.87 mmol) were combined in methylene chloride (1.5 mL) and cooled in an ice bath. O-(7-Azabenzotriazole-1-yl)-N,N,N'N'-tetramethyluronium hexafluorophosphate (110 mg, 0.29 mmol) was added and the ice bath was removed. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 50% ethyl acetate/chloroform to 80% ethyl acetate/hexanes) to afford (E)-N-[1-(3-acetylamino-benzyl)-1H-pyrazol-3-yl]-2-(3-chloro-4-methanesulfonyl-phenyl)-2-cyclopentyloxyimino-acetamide (67 mg, 42%) as a white solid after lyophilization from aqueous acetonitrile: LC-MS (ESI) m/e calcd for C$_{26}$H$_{28}$ClN$_5$O$_5$S [M$^+$] 557.15, found 558 [M+H$^+$]; H$^1$-NMR (400 MHz, CDCl$_3$) δ ppm 1.63 (m, 4 H, 2×CH$_2$), 1.84 (m, 4 H, 2×CH$_2$), 2.16 (s, 3 H, CO$_2$CH$_3$), 3.29 (s, 3 H, SO$_2$CH$_3$), 4.86 (m, 1 H, OCH), 5.20 (s, 2H, NCH$_2$), 6.75 (d, J=2.3 Hz, 1 H, Ar), 6.92 (brd, J=7.7 Hz, 1 H, Ar), 7.29 (brt, J=8.0 Hz, 1 H, Ar), 7.37 (m, 3 H, 2 Ar and NH), 7.43 (brd, J=7.9 Hz, 1 H, Ar), 7.54 (dd, Jo=8.2, Jm=1.5 Hz, 1 H, Ar), 7.64 (d, Jm=1.5 Hz, 1 H, Ar), 8.17 (d, Jo=8.2 Hz, 1 H, Ar), 9.20 (s, 1 H, NH).

Example 31

(E)-2-(3-Chloro-4-methanesulfonyl-phenyl)-2-cyclopentyloxyimino-N-(1-pyridin-3-ylmethyl-1H-pyrazol-3-yl)-acetamide

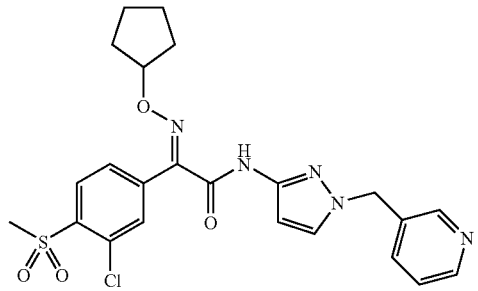

3-Nitro-1H-pyrazole (prepared as in Example 15, 113 mg, 1.00 mmol) was dissolved in N,N-dimethylformamide (5 mL) and cooled in an ice bath. A 60% suspension of sodium hydride in mineral oil (88 mg, 2.2 mmol) was added in portions and the cooling bath was removed. After stirring 1.5 h, a mixture of 3-picolyl chloride hydrochloride (164 mg, 1.00 mmol) in N,N-dimethylformamide (1 mL) was added. The reaction mixture was stirred 65 h, then evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was stirred in ethyl acetate (50 mL) and filtered. The filtrate was evaporated in vacuo and the remaining material was purified by flash column chromatography (Merck silica gel 60, 40-63 μm; (50% ethyl acetate/hexanes to 100% ethyl acetate) to afford 3-(3-nitro-pyrazol-1-ylmethyl)-pyridine (114 mg, 56%) as a clear, faintly yellow oil which began to solidify over time: LC-MS (ESI) m/e calcd for C$_9$H$_8$N$_4$O$_2$ [M$^+$] 204.06, found 205 [M+H$^+$].

3-(3-Nitro-pyrazol-1-ylmethyl)-pyridine (113 mg, 0.55 mmol) was dissolved in a mixture of methanol and ethyl acetate (1 mL each). Hydrazine (156 μL, 4.97 mmol) was added followed by a slurry of Raney nickel in water (1.5 mL) causing vigorous gas evolution. After stirring 1 h, the reaction mixture was filtered and evaporated in vacuo. The residue was purified by flash column chromatography (Merck silica gel 60, 40-63 μm; 3% methanol/chloroform) to afford 1-pyridin-3-ylmethyl-1H-pyrazol-3-ylamine (72 mg, 75%) as a white solid: LC-MS (ESI) m/e calcd for C$_9$H$_{10}$N$_4$ [M$^+$] 174.09, found 175 [M+H$^+$].

(E)-(3-Chloro-4-methanesulfonyl-phenyl)-cyclopentyloxyimino-acetic acid (prepared as in Example 1, 115 mg, 0.33 mmol), 1-pyridin-3-ylmethyl-1H-pyrazol-3-ylamine (72 mg, 0.41 mmol) and N,N-diisopropylethylamine (232 μL, 1.33 mmol) were combined in methylene chloride (1.7 mL) and cooled in an ice bath. O-(7-Azabenzotriazole-1-yl)-N,N,N'N'-tetramethyluronium hexafluorophosphate (139 mg, 0.37 mmol) was added and the ice bath was removed. After stirring 2 h, the reaction mixture was evaporated in vacuo. The residue was treated with saturated aqueous sodium bicarbonate solution (1 mL) and extracted with chloroform (2×3 mL). The combined organic phases were dried over sodium sulfate and evaporated in vacuo. The residue was purified by flash column chromatography (Merck silica gel 60, 40-63 μm; 50% ethyl acetate/chloroform to 5% methanol/chloroform) to afford (E)-2-(3-chloro-4-methanesulfonyl-phenyl)-2-cyclopentyloxyimino-N-(1-pyridin-3-ylmethyl-1H-pyrazol-3-yl)-acetamide (76 mg, 46%) as a white solid after lyophilization from aqueous dioxane: LC-MS (ESI) m/e calcd for $C_{23}H_{24}ClN_5O_4S$ [$M^+$] 501.12, found 502 [$M+H^+$]; $H^1$-NMR (400 MHz, $CDCl_3$) δ ppm 1.64 (m, 4 H, 2×$CH_2$), 1.85 (m, 4 H, 2×$CH_2$), 3.28 (s, 3 H, $SO_2CH_3$), 4.87 (m, 1 H, OCH), 5.26 (s, 2 H, $NCH_3$), 6.78 (d, J=2.3 Hz, 1 H, Ar), 7.30 (dd, J=7.9, J=4.9 Hz, 1 H, Ar), 7.40 (d, J=2.3 Hz, 1 H, Ar), 7.51 (m, 1 H, Ar), 7.55 (dd, Jo=8.2, Jm=1.6 Hz, 1 H, Ar), 7.65 (d, Jm=1.6 Hz, 1 H, Ar), 8.18 (d, Jo=8.2 Hz, 1 H, Ar), 8.56 (m, 2H, Ar), 9.17 (s, 1 H, NH).

Example 32

In Vitro Glucokinase Activity

The compounds of formula I which include the compounds set forth in the Examples activated glucokinase in vitro by the procedure of this Example. In this manner, they increase the enzymatic activity of glucokinase. Therefore, the compounds of formula I are glucokinase activators.

Glucokinase In Vitro Assay Protocol. Glucokinase (GK) was assayed by coupling the production of glucose-6-phosphate to the generation of NADH with glucose-6-phosphate dehydrogenase (G6PDH, Roche) from *Leuconostoc mesenteroides* as the coupling enzyme (Scheme 2).

Scheme 2

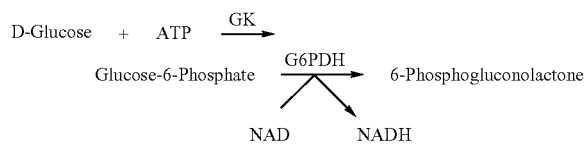

Recombinant human liver GK was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C.-30° C. in a flat bottom 96-well tissue culture plate from Costar (Cambridge, Mass.) with a final incubation volume of 120 µL. The incubation reaction contained the following: 25 mM Hepes buffer (pH 7.1), 25 mM KCl, 5 mM D-glucose, 1 mM ATP, 1.8 mM NAD, 2 mM $MgCl_2$, 1 µM sorbitol-6-phosphate, 1 mM dithiothreitol, test drug or 10% DMSO, 1.8 unit/ml G6PDH, and GK (see below). All organic reagents were >98% pure and were from Roche with the exceptions of D-glucose and Hepes which were from Sigma Chemical Co, St Louis, Mo. Test compounds were dissolved in DMSO and were added to the incubation reaction minus GST-GK in a volume of 12 µL to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µL GST-GK.

After addition of enzyme, the increase in optical density (OD) at 340 nm was monitored over a 15 minute incubation period as a measure of GK activity. The GK activity in control wells (mOD/min) was compared with the activity in wells containing test GK activators (mOD/min), and the concentration of activator that produced a 50% increase in the activity of GK, i.e., the $SC_{1.5}$, was calculated.

All of the compounds of formula I described in the Examples had an $SC_{1.5}$ less than or equal to 100 µM and the Table below provides for representative values:

| Example | $SC_{1.5}$ |
|---------|------------|
| 7       | 0.79       |
| 9       | 12         |
| 10      | 8.4        |
| 12      | 1.1        |
| 14      | 0.26       |
| 19      | 29         |
| 23      | 2.8        |
| 24      | 5.3        |
| 25      | 1.6        |
| 31      | 0.35       |

REFERENCES

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J.* 309: 167-173, 1995.

Neet, K., Keenan, R. P., and Tippett, P. S. Observation of a kinetic slow transition in monomeric glucokinase. *Biochemistry* 29; 770-777, 1990.

Example 33

In Vivo Glucokinase Activity

Glucokinase Activator in vivo Screen Protocol in Lean and Diet Induced Obese Mice: Lean or Diet-induced Obese (DIO) C57BL/6J mice were orally dosed via gavage with Glucokinase (GK) activator (50 mg/kg body weight for lean mice, 25 mg/kg body weight for DIO mice) following a two hour fasting period. Blood glucose determinations were made at various times during the six hour study period.

C57Bl/6J mice were maintained in a light-dark cycle with lights on from 0600-1800 hr. For studies in lean mice, the mice were received at age six weeks and given ad libitum access to control diet (LabDiet 5001 chow, PMI Nutrition, Brentwood, Mo.), and were at least age 11 weeks at the time of study. For studies in the DIO model, the mice were received at age five weeks and given ad libitum access to Bio-Serv F3282 High Fat Diet (Frenchtown, N.J.), and were at least age 16 weeks at the time of study. The experiments were conducted during the light phase of the light-dark cycle. Mice (n=6) are weighed and fasted for a two hour period prior to oral treatment. GK activators were formulated in Gelucire vehicle (Ethanol:Gelucire44/14:PEG400 q.s. 4:66:30 v/w/v). For studies in lean mice, the mice were dosed orally with 5.0 mL/kg of body weight with a 10.0 mg/ml formulation to equal a 50 mg/kg dose. For studies in DIO mice, the mice were dosed orally with 5.0 mL/kg of body weight with a 5 mg/mL formulation to equal a 25 mg/kg dose. Immediately prior to dosing, a pre-dose (time zero) blood glucose reading was acquired by a tail snip and collecting 15 µL blood into a heparinized capillary tube for analysis. Following GK activator administration, additional blood glucose readings were taken at 2, 4 and 6 hours post dose. Results were interpreted by comparing the mean blood glucose values of six vehicle treated mice with six GK activator treated mice over the six hour study duration. Preferred compounds were considered to be those that exhibited a statistically significant ($p \leq 0.05$) decrease in blood glucose compared to vehicle for two consecutive assay time points.

It is to be understood that the invention is not limited to the particular embodiments of the invention described above, as variations of the particular embodiments may be made and still fall within the scope of the appended claims.

What is claimed is:

1. A compound of formula (I):

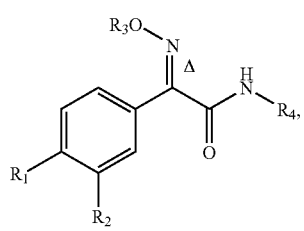

wherein:
$R_1$, $R_2$ are, independently, hydrogen, halo, amino, hydroxyamino, cyano, nitro, lower alkyl, -$OR_5$, -C(O)$OR_6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, lower alkoxy lower alkyl sulfinyl, perfluoro-lower alkyl sulfinyl or sulfonamido;
$R_3$ is cycloalkyl, having from 3 to 7 carbon atoms, or lower alkyl;
$R_4$ is benzothiazole, unsubstituted or substituted with lower alkyl, halo, alkoxy or oxo, urea, or an unsubstituted or monosubstituted five-or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, said monosubstituted heteroaromatic ring being monosubstituted at a position on a ring carbon atom or nitrogen other than adjacent to said connecting carbon atom with a substituent selected from the group consisting of lower alkyl, halo, nitro, cyano, perfluoro- lower alkyl, oxo, —(CH$_2$)$_n$—OR$_7$, —(CH$_2$)$_n$—C(O)—OR$_7$, —(CH$_2$)$_n$—C(O)—NH—R$_7$, —C(O)C(O)—OR$_7$, —(CH$_2$)$_n$—NHR$_7$, —(CH$_2$)$_m$-Ph, —(CH$_2$)$_m$—Ph—C(O)OR$_7$, —(CH$_2$)$_m$—Ph—C(O)NH$_2$, —(CH$_2$)$_m$—Ph—NH—C(O)R$_7$ or —(CH$_2$)$_m$-het;
$R_5$ is hydrogen, lower alkyl, or perfluoro-lower alkyl;
$R_6$ is lower alkyl;
$R_7$ is hydrogen or lower alkyl;
n is 0, 1, 2, 3 or 4; wherein n is not zero if a nitrogen-oxygen bond results;
m is 1, 2, 3 or 4;
het is a five- or six-membered heteroaromatic ring; and
Δ is a trans configuration across the double bond;
or a pharmaceutically acceptable salt thereof.

2. The compound according to claim 1, wherein:
$R_1$, $R_2$ are, independently, hydrogen, halo, amino, hydroxyamino, cyano, nitro, lower alkyl, —OR$_5$, —C(O)OR$_6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, lower alkoxy lower alkyl sulfinyl, perfluoro-lower alkyl sulfinyl or sulfonamido;
$R_3$ is cycloalkyl, having from 3 to 7 carbon atoms, or lower alkyl;
$R_4$ is benzothiazole, unsubstituted or substituted with lower alkyl, halo, or alkoxy;
$R_5$ is hydrogen, lower alkyl, or perfluoro-lower alkyl;
$R_6$ is lower alkyl; and
or a pharmaceutically acceptable salt thereof.

3. The compound according to claim 1, wherein:
$R_1$, $R_2$ are, independently, hydrogen, halo, amino, hydroxyamino, cyano, nitro, lower alkyl, -OR$_5$, —C(O)OR$_6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, lower alkoxy lower alkyl sulfinyl, perfluoro-lower alkyl sulfinyl or sulfonamido;
$R_3$ is cycloalkyl, having from 3 to 7 carbon atoms, or lower alkyl;
$R_4$ is an unsubstituted or monosubstituted five-or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, said monosubstituted heteroaromatic ring being monosubstituted at a position on a ring carbon atom or nitrogen other than adjacent to said connecting carbon atom with a substituent selected from the group consisting of lower alkyl, halo, nitro, cyano, perfluoro- lower alkyl, oxo, —(CH$_2$)$_n$—OR$_7$, —(CH$_2$)$_n$—C(O)—OR$_7$, —(CH$_2$)$_n$—C(O)—NH—R$_7$, —C(O)C(O)—OR$_7$, —(CH$_2$)$_n$—NHR$_7$, —(CH$_2$)$_m$-Ph, —(CH$_2$)$_m$—Ph—C(O)OR$_7$, —(CH$_2$)$_m$—Ph—C(O)NH$_2$, —(CH$_2$)$_m$—Ph—NH—C(O)R$_7$ or —(CH$_2$)$_m$-het;
$R_5$ is hydrogen, lower alkyl, or perfluoro-lower alkyl;
$R_6$ is lower alkyl;
$R_7$ is hydrogen or lower alkyl;
n is 0, 1, 2, 3 or 4; wherein n is not zero if a nitrogen-oxygen bond results;
m is 1, 2, 3 or 4; and
het is a five- or six-membered heteroaromatic ring;
or a pharmaceutically acceptable salt thereof.

4. The compound according to claim 1, wherein:
$R_1$, $R_2$ are, independently, hydrogen, halo, amino, hydroxyamino, cyano, nitro, lower alkyl, -OR$_5$, -C(O)OR$_6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, lower alkoxy lower alkyl sulfinyl, perfluoro-lower alkyl sulfinyl or sulfonamido;
$R_3$ is cycloalkyl, having from 3 to 7 carbon atoms;
$R_4$ is an unsubstituted or monosubstituted five-or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, said monosubstituted heteroaromatic ring being monosubstituted at a position on a ring carbon atom or nitrogen other than adjacent to said connecting carbon atom with a substituent selected from the group consisting of lower alkyl, halo, nitro, cyano, perfluoro- lower alkyl, oxo, —(CH$_2$)$_n$—OR$_7$, —(CH$_2$)$_n$—C(O)—OR$_7$, —(CH$_2$)$_n$—C(O)—NH—R$_7$, —C(O)C(O)—OR$_7$, —(CH$_2$)$_n$—NHR$_7$, —(CH$_2$)$_m$-Ph, —(CH$_2$)$_m$—Ph—C(O)OR$_7$, —(CH$_2$)$_m$—Ph—C(O)NH$_2$, —(CH$_2$)$_m$—Ph—NH—C(O)R$_7$ or —(CH$_2$)$_m$-het;
R$_5$ is hydrogen, lower alkyl, or perfluoro-lower alkyl;
R$_6$ is lower alkyl;
R$_7$ is hydrogen or lower alkyl;
n is 0, 1, 2, 3 or 4; wherein n is not zero if a nitrogen-oxygen bond results;
m is 1, 2, 3 or 4; and
het is a five- or six-membered heteroaromatic ring;
or a pharmaceutically acceptable salt thereof.

5. The compound according to claim 1, wherein:
R$_1$, R$_2$ are, independently, hydrogen, halo, amino, hydroxyamino, cyano, nitro, lower alkyl, —OR$_5$, —C(O)OR$_6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, lower alkoxy lower alkyl sulfinyl, perfluoro-lower alkyl sulfinyl or sulfonamido;
R$_3$ is cycloalkyl, having from 3 to 7 carbon atoms;
R$_4$ is benzothiazole, unsubstituted or substituted with lower alkyl, halo, or alkoxy;
R$_5$ is hydrogen, lower alkyl, or perfluoro-lower alkyl; and
R$_6$ is lower alkyl;
or a pharmaceutically acceptable salt thereof.

6. The compound according to claim 1, wherein:
R$_1$ is methanesulfonyl;
R$_2$ is chloro;
R$_3$ is cycloalkyl having from 3 to 7 carbon atoms; and
R$_4$ is benzothiazole, unsubstituted or substituted with lower alkyl, halo, or alkoxy;
or a pharmaceutically acceptable salt thereof.

7. The compound according to claim 1, wherein:
R$_1$ is methanesulfonyl;
R$_2$ is chloro;
R$_3$ is cycloalkyl having from 3 to 7 carbon atoms; and
R$_4$ is an unsubstituted or monosubstituted five-or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, said monosubstituted heteroaromatic ring being monosubstituted at a position on a ring carbon atom or nitrogen other than adjacent to said connecting carbon atom with a substituent selected from the group consisting of lower alkyl, halo, nitro, cyano, perfluoro- lower alkyl, oxo, —(CH$_2$)$_n$—OR$_7$, —(CH$_2$)$_n$—C(O)—OR$_7$, —(CH$_2$)$_n$—C(O)—NH—R$_7$, —C(O)C(O)—OR$_7$, —(CH$_2$)$_n$—NHR$_7$, —(CH$_2$)$_m$—Ph, —(CH$_2$)$_m$—Ph—C(O)OR$_7$, —(CH$_2$)$_m$—Ph—C(O)NH$_2$, —(CH$_2$)$_m$—Ph—NH—C(O)R$_7$ or —(CH$_2$)$_m$-het;
R$_7$ is hydrogen or lower alkyl;
n is 0, 1, 2, 3 or 4; wherein n is not zero if a nitrogen-oxygen bond results;
m is 1, 2, 3 or 4; and
het is a five- or six-membered heteroaromatic ring;
or a pharmaceutically acceptable salt thereof.

8. The compound according to claim 1, wherein said compound is E)-2-(3-Chloro-4-methanesulfonyl-phenyl)-2-cyclopentyloxyimino-N-thiazol-2-yl-acetamide.

9. The compound according to claim 1, wherein said compound is (E)-N -Benzothiazol-2-yl-2-(3-chloro-4-methanesulfonyl-phenyl)-2-isopropoxyimino-acetamide.

10. The compound according to claim 1, wherein said compound is (E)-N -Benzothiazol-2-yl-2-(3-chloro-4-methanesulfonyl-phenyl)-2-cyclopentyloxyimino-acetamide.

11. The compound according to claim 1, wherein said compound is (E)-4-{3-[2-(3-Chloro-4-methanesulfonyl-phenyl)-2-cyclopentyloxyimino-acetylamino] -pyrazol-1 -ylmethyl} -benzoic acid methyl ester.

12. The compound according to claim 1, wherein said compound is (E)-2-[2-(3-Chloro-4-methanesulfonyl-phenyl)-2-cyclopentyloxyimino-acetylamino] -thiazole-5 -carboxylic acid amide.

13. The compound according to claim 1, wherein said compound is (E) -4-{3-[2-(3-Chloro-4-methanesulfonyl-phenyl)-2-cyclopentyloxyimino-acetylamino] -pyrazol-1 -ylmethyl} -benzamide.

14. The compound according to claim 1, wherein said compound is (E)-N -Benzothiazol-2-yl-2-cyclopentyloxyimino-2-(4-methanesulfonyl-phenyl)-acetamide.

15. The compound according to claim 1, wherein said compound is (E)-2-(3-Chloro-4-methanesulfonyl-phenyl)-2-cyclopentyloxyimino-N-(5-methyl-thiazol-2-yl)-acetamide.

16. The compound according to claim 1, wherein said compound is (E)-2-(3-Chloro-4-methanesulfonyl-phenyl)-2-cyclopentyloxyimino-N-(6-methoxy-benzothiazol-2-yl)-acetamide.

17. The compound according to claim 1, wherein said compound is (E)-N-[1-(3-Acetylamino-benzyl)-1H-pyrazol-3-yl]-2-(3-chloro-4-methanesulfonyl-phenyl)-2-cyclopentyloxyimino-acetamide.

18. The compound according to claim 1, wherein said compound is (E)-2-(3-Chloro-4-methanesulfonyl-phenyl)-2-cyclopentyloxyimino-N-(1 -pyridin-3 -ylmethyl-1H-pyrazol-3 -yl) -acetamide.

19. A pharmaceutical composition, comprising a therapeutically effective amount of a compound according to claim 1 and a pharmaceutically acceptable carrier.

* * * * *